United States Patent
Chapman, Jr. et al.

(10) Patent No.: US 11,033,667 B2
(45) Date of Patent: Jun. 15, 2021

(54) SORBENT MANIFOLD FOR A DIALYSIS SYSTEM

(71) Applicant: Medtronic, Inc., Minneapolis, MN (US)

(72) Inventors: Paul R. Chapman, Jr., Lutz, FL (US); Carl Wilbert Gomes, II, Parrish, FL (US)

(73) Assignee: Medtronic, Inc., Minneapolis, MN (US)

( * ) Notice: Subject to any disclaimer, the term of this patent is extended or adjusted under 35 U.S.C. 154(b) by 230 days.

(21) Appl. No.: 16/155,916

(22) Filed: Oct. 10, 2018

(65) Prior Publication Data

US 2019/0240388 A1 Aug. 8, 2019

Related U.S. Application Data

(60) Provisional application No. 62/625,540, filed on Feb. 2, 2018.

(51) Int. Cl.
| | |
|---|---|
| *A61M 1/16* | (2006.01) |
| *A61M 1/26* | (2006.01) |
| *A61M 1/36* | (2006.01) |
| *B01D 15/00* | (2006.01) |
| *B01D 35/147* | (2006.01) |
| *B01D 35/16* | (2006.01) |
| *B01D 37/04* | (2006.01) |

(52) U.S. Cl.
CPC ........ *A61M 1/1609* (2014.02); *A61M 1/1656* (2013.01); *A61M 1/1696* (2013.01); *A61M 1/267* (2014.02); *A61M 1/3643* (2013.01); *A61M 2205/18* (2013.01); *A61M 2205/3303* (2013.01); *A61M 2205/3331* (2013.01); *A61M 2205/3368* (2013.01); *A61M 2205/75* (2013.01); *B01D 15/00* (2013.01); *B01D 35/147* (2013.01); *B01D 35/16* (2013.01); *B01D 37/04* (2013.01)

(58) Field of Classification Search
None
See application file for complete search history.

(56) References Cited

U.S. PATENT DOCUMENTS

| | | | |
|---|---|---|---|
| 3,091,098 | A | 5/1963 | Bowers |
| 3,370,710 | A | 2/1968 | Bluemle |

(Continued)

FOREIGN PATENT DOCUMENTS

| | | |
|---|---|---|
| CN | 101687070 | 3/2010 |
| CN | 101883594 A | 11/2010 |

(Continued)

OTHER PUBLICATIONS

[NPL264] PCT/US2014/014357 International Search Report and Written Opinion dated May 19, 2014.

(Continued)

*Primary Examiner* — Matthew O Savage

(57) ABSTRACT

The present invention relates to a sorbent manifold and related systems and methods having a plurality of passageways fluidly connectable to one or more valves and one or more sensors and components for use in a sorbent dialysis system. The sorbent manifold can control the one or more valves to direct fluid to either pass through a sorbent cartridge or bypass the sorbent cartridge based on measurements obtained from sensors.

14 Claims, 8 Drawing Sheets

(56) References Cited

U.S. PATENT DOCUMENTS

| | | |
|---|---|---|
| 3,506,126 A | 4/1970 | Lindsay, Jr. |
| 3,608,729 A | 9/1971 | Haselden |
| 3,669,878 A | 6/1972 | Marantz |
| 3,669,880 A | 6/1972 | Marantz |
| 3,692,648 A | 9/1972 | Matloff |
| 3,776,819 A | 12/1973 | Williams |
| 3,809,241 A | 5/1974 | Alvine |
| 3,850,835 A | 11/1974 | Marantz |
| 3,884,808 A | 5/1975 | Scott |
| 3,902,490 A | 9/1975 | Jacobsen |
| 3,939,069 A | 2/1976 | Granger |
| 3,989,622 A | 11/1976 | Marantz |
| 4,060,485 A | 11/1977 | Eaton |
| 4,094,775 A | 6/1978 | Mueller |
| 4,136,708 A | 1/1979 | Cosentino |
| 4,142,845 A | 3/1979 | Lepp |
| 4,201,555 A | 5/1980 | Tkach |
| 4,209,392 A | 6/1980 | Wallace |
| 4,269,708 A | 5/1981 | Bonomini |
| 4,316,725 A | 2/1982 | Hovind |
| 4,371,385 A | 2/1983 | Johnson |
| 4,374,382 A | 2/1983 | Markowitz |
| 4,376,707 A | 3/1983 | Lehmann |
| 4,381,999 A | 5/1983 | Boucher |
| 4,430,098 A | 2/1984 | Bowman |
| 4,460,555 A | 7/1984 | Thompson |
| 4,490,135 A | 12/1984 | Troutner |
| 4,556,063 A | 12/1985 | Thompson |
| 4,562,751 A | 1/1986 | Nason |
| 4,581,141 A | 4/1986 | Ash |
| 4,612,122 A | 9/1986 | Ambrus |
| 4,650,587 A | 3/1987 | Polak |
| 4,678,408 A | 7/1987 | Mason |
| 4,685,903 A | 8/1987 | Cable |
| 4,695,385 A | 9/1987 | Boag |
| 4,715,398 A | 12/1987 | Shouldice |
| 4,747,822 A | 5/1988 | Peabody |
| 4,750,494 A | 6/1988 | King |
| 4,816,162 A | 3/1989 | Rosskopf et al. |
| 4,826,663 A | 5/1989 | Alberti |
| 4,828,693 A | 5/1989 | Lindsay |
| 4,885,001 A | 12/1989 | Leppert |
| 4,900,308 A | 2/1990 | Verkaart |
| 4,915,713 A | 4/1990 | Buzza |
| 4,950,230 A | 8/1990 | Kendell |
| 4,977,888 A | 12/1990 | Rietter |
| 5,015,388 A | 5/1991 | Pusineri |
| 5,032,265 A | 7/1991 | Jha |
| 5,080,653 A | 1/1992 | Voss |
| 5,092,886 A | 3/1992 | Dobos-Hardy |
| 5,097,122 A | 3/1992 | Coiman |
| 5,114,580 A | 5/1992 | Ahmad |
| 5,127,404 A | 7/1992 | Wyborny |
| 5,141,493 A | 8/1992 | Jacobsen |
| 5,180,403 A | 1/1993 | Kogure |
| 5,192,132 A | 3/1993 | Pelensky |
| 5,230,702 A | 7/1993 | Lindsay |
| 5,284,470 A | 2/1994 | Beltz |
| 5,302,288 A | 4/1994 | Meidl |
| 5,305,745 A | 4/1994 | Zacouto |
| 5,308,315 A | 5/1994 | Khuri |
| 5,318,750 A | 6/1994 | Lascombes |
| 5,399,157 A | 3/1995 | Goux |
| 5,419,347 A | 5/1995 | Carruth |
| 5,441,049 A | 8/1995 | Masano |
| 5,442,969 A | 8/1995 | Troutner |
| 5,468,388 A | 11/1995 | Goddard |
| 5,507,723 A | 4/1996 | Keshaviah |
| 5,591,344 A | 1/1997 | Kenley |
| 5,643,201 A | 7/1997 | Peabody |
| 5,662,806 A | 9/1997 | Keshaviah et al. |
| 5,683,432 A | 11/1997 | Goedeke |
| 5,685,835 A | 11/1997 | Brugger |
| 5,685,988 A | 11/1997 | Malchesky |
| 5,702,536 A | 12/1997 | Carruth |
| 5,744,031 A | 4/1998 | Bene |
| 5,762,782 A | 6/1998 | Kenley |
| 5,849,179 A | 12/1998 | Emerson |
| 5,858,186 A | 1/1999 | Glass |
| 5,863,421 A | 1/1999 | Peter |
| 5,938,938 A | 8/1999 | Bosetto |
| 5,944,684 A | 8/1999 | Roberts |
| 5,948,251 A | 9/1999 | Brugger |
| 6,048,732 A | 4/2000 | Anslyn |
| 6,052,622 A | 4/2000 | Holmstrom |
| 6,058,331 A | 5/2000 | King |
| 6,114,176 A | 9/2000 | Edgson et al. |
| 6,126,831 A | 10/2000 | Goldau |
| 6,171,480 B1 | 1/2001 | Lee |
| 6,230,059 B1 | 5/2001 | Duffin |
| 6,248,093 B1 | 6/2001 | Moberg |
| 6,251,167 B1 | 6/2001 | Berson |
| 6,254,567 B1 | 7/2001 | Treu |
| 6,264,680 B1 | 7/2001 | Ash |
| 6,321,101 B1 | 11/2001 | Holmstrom |
| 6,362,591 B1 | 3/2002 | Moberg |
| 6,363,279 B1 | 3/2002 | Ben-Haim |
| 6,521,184 B1 | 2/2003 | Edgson et al. |
| 6,554,798 B1 | 4/2003 | Mann |
| 6,555,986 B2 | 4/2003 | Moberg |
| 6,589,229 B1 | 7/2003 | Connelly |
| 6,593,747 B2 | 7/2003 | Puskas |
| 6,602,399 B1 | 8/2003 | Fromherz |
| 6,627,164 B1 | 9/2003 | Wong |
| 6,666,840 B1 | 12/2003 | Falkvall et al. |
| 6,676,608 B1 | 1/2004 | Keren |
| 6,711,439 B1 | 3/2004 | Bradley |
| 6,719,745 B1 | 4/2004 | Taylor |
| 6,726,647 B1 | 4/2004 | Sternby |
| 6,780,322 B1 | 8/2004 | Bissler |
| 6,814,724 B2 | 11/2004 | Taylor |
| 6,818,196 B2 | 11/2004 | Wong |
| 6,824,524 B1 | 11/2004 | Favre |
| 6,861,266 B1 | 3/2005 | Sternby |
| 6,878,283 B2 | 4/2005 | Thompson |
| 6,960,179 B2 | 11/2005 | Gura |
| 7,023,359 B2 | 4/2006 | Goetz |
| 7,033,498 B2 | 4/2006 | Wong |
| 7,074,332 B2 | 7/2006 | Summerton |
| 7,077,819 B1 | 7/2006 | Goldau |
| 7,097,630 B2 | 8/2006 | Gotch |
| 7,101,519 B2 | 9/2006 | Wong |
| 7,153,693 B2 | 12/2006 | Tajiri |
| 7,169,303 B2 | 1/2007 | Sullivan |
| 7,208,092 B2 | 4/2007 | Micheli |
| 7,241,272 B2 | 7/2007 | Karoor |
| 7,276,042 B2 | 10/2007 | Polaschegg |
| 7,279,031 B1 | 10/2007 | Wright |
| 7,318,892 B2 | 1/2008 | Connell |
| 7,326,576 B2 | 2/2008 | Womble et al. |
| 7,435,342 B2 | 10/2008 | Tsukamoto |
| 7,488,447 B2 | 2/2009 | Sternby |
| 7,500,958 B2 | 3/2009 | Asbrink |
| 7,537,688 B2 | 5/2009 | Tarumi |
| 7,544,300 B2 | 6/2009 | Brugger |
| 7,544,737 B2 | 6/2009 | Poss |
| 7,563,240 B2 | 7/2009 | Gross |
| 7,566,432 B2 | 7/2009 | Wong |
| 7,575,564 B2 | 8/2009 | Childers |
| 7,597,806 B2 | 10/2009 | Uchi |
| 7,674,231 B2 | 3/2010 | McCombie |
| 7,704,361 B2 | 4/2010 | Garde |
| 7,736,507 B2 | 6/2010 | Wong |
| 7,744,553 B2 | 6/2010 | Kelly |
| 7,754,852 B2 | 7/2010 | Burnett |
| 7,756,572 B1 | 7/2010 | Fard |
| 7,776,210 B2 | 8/2010 | Rosenbaum |
| 7,785,463 B2 | 8/2010 | Bissler |
| 7,790,103 B2 | 9/2010 | Shah |
| 7,794,141 B2 | 9/2010 | Perry |
| 7,794,419 B2 | 9/2010 | Paolini |
| 7,850,635 B2 | 12/2010 | Polaschegg |
| 7,857,976 B2 | 12/2010 | Bissler |
| 7,867,214 B2 | 1/2011 | Childers |

(56) References Cited

U.S. PATENT DOCUMENTS

| | | |
|---|---|---|
| 7,896,831 B2 | 3/2011 | Sternby |
| 7,922,686 B2 | 4/2011 | Childers |
| 7,922,911 B2 | 4/2011 | Micheli |
| 7,947,179 B2 | 5/2011 | Rosenbaum |
| 7,955,290 B2 | 6/2011 | Karoor |
| 7,955,291 B2 | 6/2011 | Sternby |
| 7,967,022 B2 | 6/2011 | Grant |
| 7,981,082 B2 | 7/2011 | Wang |
| 7,988,854 B2 | 8/2011 | Tsukamoto |
| 8,002,726 B2 | 8/2011 | Karoor |
| 8,029,454 B2 | 10/2011 | Kelly |
| 8,034,161 B2 | 10/2011 | Gura |
| 8,066,658 B2 | 11/2011 | Karoor |
| 8,070,709 B2 | 12/2011 | Childers |
| 8,080,161 B2 | 12/2011 | Ding et al. |
| 8,087,303 B2 | 1/2012 | Beavis |
| 8,096,969 B2 | 1/2012 | Roberts |
| 8,137,553 B2 | 3/2012 | Fulkerson |
| 8,180,574 B2 | 5/2012 | Lo |
| 8,183,046 B2 | 5/2012 | Lu |
| 8,187,250 B2 | 5/2012 | Roberts |
| 8,197,439 B2 | 6/2012 | Wang |
| 8,202,241 B2 | 6/2012 | Karakama |
| 8,246,826 B2 | 8/2012 | Wilt |
| 8,273,049 B2 | 9/2012 | Demers |
| 8,292,594 B2 | 10/2012 | Tracey |
| 8,303,532 B2 | 11/2012 | Hamada |
| 8,313,642 B2 | 11/2012 | Yu |
| 8,317,492 B2 | 11/2012 | Demers |
| 8,357,113 B2 | 1/2013 | Childers |
| 8,366,316 B2 | 2/2013 | Kamen |
| 8,366,655 B2 | 2/2013 | Kamen |
| 8,404,491 B2 | 3/2013 | Li |
| 8,409,441 B2 | 4/2013 | Wilt |
| 8,409,444 B2 | 4/2013 | Wong |
| 8,491,517 B2 | 7/2013 | Karoor |
| 8,496,809 B2 | 7/2013 | Roger |
| 8,499,780 B2 | 8/2013 | Wilt |
| 8,500,672 B2 | 8/2013 | Caleffi |
| 8,500,676 B2 | 8/2013 | Jansson |
| 8,500,994 B2 | 8/2013 | Weaver |
| 8,512,271 B2 | 8/2013 | Moissl |
| 8,518,258 B2 | 8/2013 | Balschat |
| 8,518,260 B2 | 8/2013 | Raimann |
| 8,521,482 B2 | 8/2013 | Akonur |
| 8,535,525 B2 | 9/2013 | Heyes |
| 8,560,510 B2 | 10/2013 | Brueggerhoff |
| 8,562,822 B2 | 10/2013 | Roger |
| 8,580,112 B2 | 11/2013 | Updyke |
| 8,597,227 B2 | 12/2013 | Childers |
| 8,696,626 B2 | 4/2014 | Kirsch |
| 8,777,892 B2 | 7/2014 | Sandford |
| 8,903,492 B2 | 12/2014 | Soykan |
| 8,906,240 B2 | 12/2014 | Crnkovich |
| 9,144,640 B2 | 9/2015 | Pudil |
| 9,173,987 B2 | 11/2015 | Meyer |
| 2002/0027106 A1 | 3/2002 | Smith |
| 2002/0042561 A1 | 4/2002 | Schulman |
| 2002/0045851 A1 | 4/2002 | Suzuki |
| 2002/0104800 A1 | 8/2002 | Collins |
| 2002/0112609 A1 | 8/2002 | Wong |
| 2003/0010717 A1 | 1/2003 | Brugger |
| 2003/0080059 A1 | 5/2003 | Peterson |
| 2003/0097086 A1 | 5/2003 | Gura |
| 2003/0105424 A1 | 6/2003 | Karoor |
| 2003/0105435 A1 | 6/2003 | Taylor |
| 2003/0114787 A1 | 6/2003 | Gura |
| 2004/0019312 A1 | 1/2004 | Childers |
| 2004/0019320 A1 | 1/2004 | Childers |
| 2004/0068219 A1 | 4/2004 | Summerton |
| 2004/0082903 A1 | 4/2004 | Micheli |
| 2004/0099593 A1 | 5/2004 | DePaolis |
| 2004/0102732 A1 | 5/2004 | Naghavi |
| 2004/0143173 A1 | 7/2004 | Reghabi |
| 2004/0147900 A1 | 7/2004 | Polaschegg |
| 2004/0168969 A1 | 9/2004 | Sternby |
| 2004/0215090 A1 | 10/2004 | Erkkila |
| 2005/0006296 A1 | 1/2005 | Sullivan |
| 2005/0065760 A1 | 3/2005 | Murtfeldt |
| 2005/0101901 A1 | 5/2005 | Gura |
| 2005/0113796 A1 | 5/2005 | Taylor |
| 2005/0115898 A1 | 6/2005 | Sternby |
| 2005/0126961 A1 | 6/2005 | Bissler |
| 2005/0131331 A1 | 6/2005 | Kelly |
| 2005/0131332 A1 | 6/2005 | Kelly |
| 2005/0153904 A1 | 6/2005 | Fager |
| 2005/0126998 A1 | 7/2005 | Childers |
| 2005/0148923 A1 | 7/2005 | Sternby |
| 2005/0150832 A1 | 7/2005 | Tsukamoto |
| 2005/0234381 A1 | 10/2005 | Niemetz |
| 2005/0274658 A1 | 12/2005 | Rosenbaum |
| 2006/0025661 A1 | 2/2006 | Sweeney |
| 2006/0217771 A1 | 2/2006 | Soykan |
| 2006/0054489 A1 | 3/2006 | Denes |
| 2006/0076295 A1 | 4/2006 | Leonard |
| 2006/0157335 A1 | 7/2006 | Levine |
| 2006/0157413 A1 | 7/2006 | Bene |
| 2006/0186044 A1 | 8/2006 | Nalesso |
| 2006/0195064 A1 | 8/2006 | Plahey |
| 2006/0226079 A1 | 10/2006 | Mori |
| 2006/0241709 A1 | 10/2006 | Soykan |
| 2006/0264894 A1 | 11/2006 | Moberg |
| 2007/0007208 A1 | 1/2007 | Brugger |
| 2007/0066928 A1 | 3/2007 | Lannoy |
| 2007/0072285 A1 | 3/2007 | Barringer |
| 2007/0138011 A1 | 6/2007 | Hofmann |
| 2007/0175827 A1 | 8/2007 | Wariar |
| 2007/0179431 A1 | 8/2007 | Roberts |
| 2007/0213653 A1 | 9/2007 | Childers |
| 2007/0213665 A1 | 9/2007 | Curtin |
| 2007/0215545 A1 | 9/2007 | Bissler |
| 2007/0243113 A1 | 10/2007 | DiLeo |
| 2007/0255250 A1 | 11/2007 | Moberg |
| 2008/0006570 A1 | 1/2008 | Gura |
| 2008/0015493 A1 | 1/2008 | Childers et al. |
| 2008/0021337 A1 | 1/2008 | Li |
| 2008/0051696 A1 | 2/2008 | Curtin |
| 2008/0053905 A9 | 3/2008 | Brugger |
| 2008/0067132 A1 | 3/2008 | Ross |
| 2008/0093276 A1 | 4/2008 | Roger |
| 2008/0154543 A1 | 6/2008 | Rajagopal |
| 2008/0215247 A1 | 9/2008 | Tonelli |
| 2008/0217245 A1 | 9/2008 | Rambod |
| 2008/0230473 A1 | 9/2008 | Herbst |
| 2008/0253427 A1 | 10/2008 | Kamen |
| 2009/0012450 A1 | 1/2009 | Shah |
| 2009/0020471 A1 | 1/2009 | Tsukamoto |
| 2009/0078636 A1 | 3/2009 | Uchi |
| 2009/0084199 A1 | 4/2009 | Wright |
| 2009/0084721 A1 | 4/2009 | Yardimci |
| 2009/0101549 A1 | 4/2009 | Kamen |
| 2009/0101552 A1 | 4/2009 | Fulkerson |
| 2009/0101577 A1 | 4/2009 | Fulkerson |
| 2009/0105629 A1 | 4/2009 | Grant |
| 2009/0107335 A1 | 4/2009 | Wilt |
| 2009/0120864 A1 | 5/2009 | Fulkerson |
| 2009/0124963 A1 | 5/2009 | Hogard |
| 2009/0127193 A1 | 5/2009 | Updyke |
| 2009/0131858 A1 | 5/2009 | Fissell |
| 2009/0159527 A1 | 6/2009 | Mickols |
| 2009/0171261 A1 | 7/2009 | Sternby |
| 2009/0173682 A1 | 7/2009 | Robinson |
| 2009/0182263 A1 | 7/2009 | Burbank |
| 2009/0187138 A1 | 7/2009 | Lundtveit |
| 2009/0216045 A1 | 8/2009 | Singh |
| 2009/0223539 A1 | 9/2009 | Gibbel |
| 2009/0275849 A1 | 11/2009 | Stewart |
| 2009/0275883 A1 | 11/2009 | Chapman |
| 2009/0281484 A1 | 11/2009 | Childers |
| 2009/0282980 A1 | 11/2009 | Gura |
| 2009/0314063 A1 | 12/2009 | Sternby |
| 2010/0004588 A1 | 1/2010 | Yeh |
| 2010/0007838 A1 | 1/2010 | Fujimoto |
| 2010/0010429 A1 | 1/2010 | Childers |

(56) References Cited

U.S. PATENT DOCUMENTS

| | | |
|---|---|---|
| 2010/0022936 A1 | 1/2010 | Gura |
| 2010/0030151 A1 | 2/2010 | Kirsch |
| 2010/0042035 A1 | 2/2010 | Moissl |
| 2010/0051552 A1 | 3/2010 | Rohde |
| 2010/0078092 A1 | 4/2010 | Weilhoefer |
| 2010/0078381 A1 | 4/2010 | Merchant |
| 2010/0078387 A1 | 4/2010 | Wong |
| 2010/0084330 A1 | 4/2010 | Wong |
| 2010/0087771 A1 | 4/2010 | Karakama |
| 2010/0094158 A1 | 4/2010 | Solem |
| 2010/0100027 A1 | 4/2010 | Schilthuizen |
| 2010/0102190 A1 | 4/2010 | Zhu et al. |
| 2010/0106071 A1 | 4/2010 | Wallenborg |
| 2010/0114012 A1 | 5/2010 | Sandford |
| 2010/0130906 A1 | 5/2010 | Balschat |
| 2010/0137693 A1 | 6/2010 | Porras |
| 2010/0137782 A1 | 6/2010 | Jansson |
| 2010/0140149 A1 | 6/2010 | Fulkerson |
| 2010/0168546 A1 | 7/2010 | Kamath |
| 2010/0192686 A1 | 8/2010 | Kamen |
| 2010/0199670 A1 | 8/2010 | Robertson |
| 2010/0213127 A1 | 8/2010 | Castellarnau |
| 2010/0217180 A1 | 8/2010 | Akonur |
| 2010/0217181 A1 | 8/2010 | Roberts |
| 2010/0224492 A1 | 9/2010 | Ding |
| 2010/0234795 A1 | 9/2010 | Wallenas |
| 2010/0241045 A1 | 9/2010 | Kelly |
| 2010/0252490 A1 | 10/2010 | Fulkerson |
| 2010/0274171 A1 | 10/2010 | Caleffi |
| 2010/0282662 A1 | 11/2010 | Lee |
| 2010/0312172 A1 | 12/2010 | Hoffman |
| 2010/0312174 A1 | 12/2010 | Hoffman |
| 2010/0326911 A1 | 12/2010 | Rosenbaum |
| 2010/0327586 A1 | 12/2010 | Mardirossian |
| 2011/0009798 A1 | 1/2011 | Kelly |
| 2011/0017665 A1 | 1/2011 | Updyke |
| 2011/0048949 A1 | 3/2011 | Ding et al. |
| 2011/0066043 A1 | 3/2011 | Banet |
| 2011/0071465 A1 | 3/2011 | Wang |
| 2011/0077574 A1 | 3/2011 | Sigg |
| 2011/0079558 A1 | 4/2011 | Raimann |
| 2011/0087187 A1 | 4/2011 | Beck |
| 2011/0100909 A1 | 5/2011 | Stange |
| 2011/0105983 A1 | 5/2011 | Kelly |
| 2011/0106003 A1 | 5/2011 | Childers |
| 2011/0120930 A1 | 5/2011 | Mishkin |
| 2011/0120946 A1 | 5/2011 | Levin |
| 2011/0130666 A1 | 6/2011 | Dong |
| 2011/0132838 A1 | 6/2011 | Curtis |
| 2011/0144570 A1 | 6/2011 | Childers |
| 2011/0160637 A1 | 6/2011 | Beiriger |
| 2011/0163030 A1 | 7/2011 | Weaver |
| 2011/0163034 A1 | 7/2011 | Castellarnau |
| 2011/0184340 A1 | 7/2011 | Tan |
| 2011/0189048 A1 | 8/2011 | Curtis |
| 2011/0220562 A1 | 9/2011 | Beiriger |
| 2011/0247973 A1 | 10/2011 | Sargand |
| 2011/0272337 A1 | 11/2011 | Palmer |
| 2011/0284377 A1 | 11/2011 | Rohde |
| 2011/0297593 A1 | 12/2011 | Kelly |
| 2011/0315611 A1 | 12/2011 | Fulkerson |
| 2011/0315632 A1 | 12/2011 | Freije |
| 2012/0006762 A1 | 1/2012 | McCabe |
| 2012/0016228 A1 | 1/2012 | Kroh |
| 2012/0031825 A1 | 2/2012 | Gura |
| 2012/0083729 A1 | 4/2012 | Childers |
| 2012/0085707 A1 | 4/2012 | Beiriger |
| 2012/0092025 A1 | 4/2012 | Volker |
| 2012/0115248 A1 | 5/2012 | Ansyln |
| 2012/0199205 A1 | 8/2012 | Eyrard |
| 2012/0220528 A1 | 8/2012 | VanAntwerp |
| 2012/0220926 A1 | 8/2012 | Soykan |
| 2012/0234770 A1* | 9/2012 | Goodwin ............ B01D 35/147 |
| | | 210/739 |
| 2012/0248017 A1 | 10/2012 | Beiriger |
| 2012/0258545 A1 | 10/2012 | Ash |
| 2012/0258546 A1 | 10/2012 | Marran |
| 2012/0259276 A1 | 10/2012 | Childers |
| 2012/0273354 A1 | 11/2012 | Orhan et al. |
| 2012/0273415 A1 | 11/2012 | Gerber |
| 2012/0273420 A1 | 11/2012 | Gerber |
| 2012/0277546 A1 | 11/2012 | Soykan |
| 2012/0277552 A1 | 11/2012 | Gerber |
| 2012/0277604 A1 | 11/2012 | Gerber |
| 2012/0277650 A1 | 11/2012 | Gerber |
| 2012/0277655 A1 | 11/2012 | Gerber |
| 2012/0277722 A1 | 11/2012 | Gerber |
| 2012/0302945 A1 | 11/2012 | Hedmann |
| 2013/0001165 A1 | 1/2013 | Pohlmeier |
| 2013/0015302 A1 | 1/2013 | Gkhan rter |
| 2013/0018301 A1 | 1/2013 | Weaver |
| 2013/0019994 A1 | 1/2013 | Schaer |
| 2013/0030356 A1 | 1/2013 | Ding |
| 2013/0037465 A1 | 2/2013 | Heyes |
| 2013/0062265 A1 | 3/2013 | Balschat |
| 2013/0193073 A1 | 8/2013 | Hogard |
| 2013/0199998 A1 | 8/2013 | Kelly |
| 2013/0211730 A1 | 8/2013 | Wolff |
| 2013/0213890 A1 | 8/2013 | Kelly |
| 2013/0228516 A1 | 9/2013 | Jonsson |
| 2013/0228517 A1 | 9/2013 | Roger |
| 2013/0231607 A1 | 9/2013 | Roger |
| 2013/0248426 A1 | 9/2013 | Pouchoulin |
| 2013/0256227 A1 | 10/2013 | Kelly |
| 2013/0274642 A1 | 10/2013 | Soykan |
| 2013/0304020 A1 | 11/2013 | Wilt |
| 2013/0324915 A1 | 12/2013 | (Krensky)Britton |
| 2013/0330208 A1 | 12/2013 | Ly |
| 2013/0331774 A1 | 12/2013 | Farrell |
| 2014/0001112 A1 | 1/2014 | Karoor |
| 2014/0018727 A1 | 1/2014 | Burbank et al. |
| 2014/0018728 A1 | 1/2014 | Plahey |
| 2014/0042092 A1 | 2/2014 | Akonur |
| 2014/0065950 A1 | 3/2014 | Mendelsohn |
| 2014/0088442 A1 | 3/2014 | Soykan |
| 2014/0110340 A1 | 4/2014 | White |
| 2014/0110341 A1 | 4/2014 | White |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0190885 A1 | 7/2014 | Meyer |
| 2014/0190886 A1 | 7/2014 | Pudil |
| 2014/0190891 A1 | 7/2014 | Lura |
| 2014/0216250 A1 | 8/2014 | Meyer |
| 2014/0217020 A1 | 8/2014 | Meyer |
| 2014/0217027 A1 | 8/2014 | Meyer |
| 2014/0217028 A1 | 8/2014 | Pudil |
| 2014/0217029 A1 | 8/2014 | Meyer |
| 2014/0217030 A1 | 8/2014 | Meyer |
| 2014/0220699 A1 | 8/2014 | Pudil |
| 2014/0224736 A1 | 8/2014 | Heide |
| 2014/0251908 A1 | 9/2014 | Ding |
| 2015/0057602 A1 | 2/2015 | Mason |
| 2015/0083647 A1 | 3/2015 | Meyer |
| 2015/0114891 A1 | 4/2015 | Meyer |
| 2015/0144539 A1 | 5/2015 | Pudil |
| 2015/0144542 A1 | 5/2015 | Pudil |
| 2015/0157960 A1 | 6/2015 | Pudil |
| 2015/0238673 A1 | 8/2015 | Gerber |
| 2015/0250937 A1 | 9/2015 | Pudil |
| 2015/0258268 A1 | 9/2015 | Collier |
| 2015/0352270 A1 | 12/2015 | Pudil |
| 2015/0367057 A1* | 12/2015 | Gerber ............... A61M 1/1696 |
| | | 210/739 |
| 2016/0038666 A1 | 2/2016 | Kelly |
| 2016/0166748 A1 | 6/2016 | Meyer |
| 2016/0166751 A1 | 6/2016 | Meyer |

(56) References Cited

U.S. PATENT DOCUMENTS

| | | |
|---|---|---|
| 2016/0166752 A1 | 6/2016 | Meyer |
| 2016/0166753 A1 | 6/2016 | Meyer |
| 2017/0281847 A1 | 10/2017 | Venkatesh |

FOREIGN PATENT DOCUMENTS

| | | |
|---|---|---|
| CN | 102307650 | 1/2012 |
| CN | 202105667 | 1/2012 |
| CN | 101237918 | 1/2013 |
| CN | 101883584 | 7/2013 |
| CN | 103889481 A1 | 6/2014 |
| DE | 102011052188 | 1/2013 |
| EP | 0022370 A1 | 1/1981 |
| EP | 0187109 | 7/1986 |
| EP | 0264695 | 4/1988 |
| EP | 0298587 | 6/1994 |
| EP | 0743071 | 11/1996 |
| EP | 711182 B1 | 6/2003 |
| EP | 2308526 | 10/2003 |
| EP | 0906768 B1 | 2/2004 |
| EP | 1691863 | 4/2005 |
| EP | 2116269 | 2/2008 |
| EP | 1450879 | 10/2008 |
| EP | 1514562 | 4/2009 |
| EP | 1490129 | 9/2009 |
| EP | 2100553 | 8/2011 |
| EP | 2388030 | 11/2011 |
| EP | 1345856 B1 | 3/2013 |
| EP | 2344220 B1 | 4/2013 |
| EP | 1351756 | 7/2013 |
| EP | 2190498 | 7/2013 |
| EP | 1414543 | 9/2013 |
| EP | 2701596 | 3/2014 |
| EP | 2740502 | 6/2014 |
| EP | 2883558 | 6/2015 |
| EP | 1787666 | 11/2015 |
| JP | 08504116 | 5/1996 |
| JP | 2002306904 | 10/2002 |
| JP | 2006325668 A | 12/2006 |
| JP | 5099464 | 10/2012 |
| JP | 2013521862 | 6/2013 |
| WO | 9532010 A1 | 11/1995 |
| WO | 1996040313 | 12/1996 |
| WO | 9937342 A1 | 7/1999 |
| WO | 0057935 | 10/2000 |
| WO | 200066197 A1 | 11/2000 |
| WO | 2000066197 | 11/2000 |
| WO | 200170307 A1 | 9/2001 |
| WO | 2001085295 A2 | 9/2001 |
| WO | 0185295 A2 | 11/2001 |
| WO | 2002043859 | 6/2002 |
| WO | 2003043677 A2 | 5/2003 |
| WO | 2003043680 | 5/2003 |
| WO | 2003051422 A2 | 6/2003 |
| WO | 2004008826 | 1/2004 |
| WO | 2004009156 | 1/2004 |
| WO | 2004030716 A2 | 4/2004 |
| WO | 2004064616 A2 | 8/2004 |
| WO | 2004062710 A3 | 10/2004 |
| WO | 2004105589 A2 | 12/2004 |
| WO | 2004105589 A3 | 6/2005 |
| WO | 2005061026 | 7/2005 |
| WO | 2005123230 | 12/2005 |
| WO | 2005123230 A2 | 12/2005 |
| WO | 2006023589 | 3/2006 |
| WO | 2006124431 A2 | 11/2006 |
| WO | 2007010164 A2 | 1/2007 |
| WO | 2007089855 A2 | 8/2007 |
| WO | 2007146162 A2 | 12/2007 |
| WO | 2007146162 A3 | 12/2007 |
| WO | 2008037410 | 4/2008 |
| WO | 2008051994 | 5/2008 |
| WO | 2009026603 | 12/2008 |
| WO | 2009024566 | 2/2009 |
| WO | 2009026603 A1 | 3/2009 |
| WO | 2009061608 | 5/2009 |
| WO | 2009064984 | 5/2009 |
| WO | 2009067071 A1 | 5/2009 |
| WO | 2009071103 | 6/2009 |
| WO | WO 2009/073567 | 6/2009 |
| WO | 2009094184 | 7/2009 |
| WO | 2009132839 A1 | 11/2009 |
| WO | 2009157877 A1 | 12/2009 |
| WO | 2009157878 A1 | 12/2009 |
| WO | 2010028860 | 3/2010 |
| WO | 2010042666 | 4/2010 |
| WO | 2010042666 A2 | 4/2010 |
| WO | 2010052705 A1 | 5/2010 |
| WO | 2010062698 | 6/2010 |
| WO | 2010096659 | 10/2010 |
| WO | 2010121820 | 10/2010 |
| WO | 2011017215 A1 | 2/2011 |
| WO | 2011025705 A1 | 3/2011 |
| WO | 2011072337 | 8/2011 |
| WO | 2011113572 A1 | 9/2011 |
| WO | WO 2011/112317 | 9/2011 |
| WO | 2012026978 | 3/2012 |
| WO | 2012042323 | 4/2012 |
| WO | 2012050781 | 4/2012 |
| WO | 2012051996 | 4/2012 |
| WO | 2012067585 | 5/2012 |
| WO | 2010042666 A3 | 6/2012 |
| WO | 2012138604 A2 | 10/2012 |
| WO | 2012148781 | 11/2012 |
| WO | 2012148786 | 11/2012 |
| WO | 2012148789 | 11/2012 |
| WO | 2012162515 A2 | 11/2012 |
| WO | 2012172398 | 12/2012 |
| WO | 2013019179 A1 | 2/2013 |
| WO | 2013019994 A2 | 2/2013 |
| WO | 2013025844 | 2/2013 |
| WO | 2013025844 A2 | 2/2013 |
| WO | 2013028809 A2 | 2/2013 |
| WO | 2013028809 A3 | 2/2013 |
| WO | 2013019994 A3 | 4/2013 |
| WO | 2013025844 A3 | 5/2013 |
| WO | 2013103607 A1 | 7/2013 |
| WO | 2013103906 | 7/2013 |
| WO | 2013110906 | 8/2013 |
| WO | 2013110919 | 8/2013 |
| WO | 2013114063 A1 | 8/2013 |
| WO | 2013121162 A1 | 8/2013 |
| WO | 2013140346 | 9/2013 |
| WO | 2013141896 | 9/2013 |
| WO | 2013188861 A1 | 12/2013 |
| WO | 14066254 | 5/2014 |
| WO | 14066255 | 5/2014 |
| WO | 14077082 | 5/2014 |
| WO | WO 2014/099631 | 6/2014 |
| WO | 2014117000 | 7/2014 |
| WO | 2014121158 A1 | 8/2014 |
| WO | 2014121162 | 8/2014 |
| WO | 2014121163 | 8/2014 |
| WO | 2014121167 | 8/2014 |
| WO | 2014121169 | 8/2014 |
| WO | WO 2014/159918 | 10/2014 |
| WO | 2015071247 A1 | 5/2015 |
| WO | WO2017001358 | 1/2017 |

OTHER PUBLICATIONS

[NPL268] Ronco et al. 2008, Cardiorenal Syndrome, Journal American College Cardiology, 52:1527-1539, Abstract.

[NPL26] Overgaard, et. al., Activity-induced recovery of excitability in K+-depressed rat soleus muscle, Am. J. P 280: R48-R55, Jan. 1, 2001.

[NPL27] Overgaard. et. al., Relations between excitability and contractility in rate soleusmuscle: role of the NA+-K+ pump and Na+-K-S gradients. Journal of Physiology, 1999, 215-225, 518(1).

[NPL306] Coast, et al. 1990, An approach to Cardiac Arrhythmia analysis Using Hidden Markov Models, IEEE Transactions on Biomedical Engineering. 1990, 37(9):826-835.

(56) References Cited

OTHER PUBLICATIONS

[NPL309] Weiner, et. al., Article: Cardiac Function and Cardiovascular Disease in Chronic Kidney Disease, Book: Primer on Kidney Diseases (Author: Greenberg, et al), 2009,499-505, 5th Ed., Saunders Elsevier, Philadelphia, PA.
[NPL310] U.S. Appl. No. 61/480,532.
[NPL311] U.S. Appl. No. 13/424,479.
[NPL312] U.S. Appl. No: 13/424,429 dated Nov. 1, 2012.
[NPL313] U.S. Appl. No. 13/424,525.
[NPL317] U.S. Appl. No. 61/480,530.
[NPL318] U.S. Appl. No. 61/480,528 dated Apr. 29, 2011.
[NPL32] Secemsky, et. al, High prevalence of cardiac autonomic dysfunction and T-wave alternans in dialysis patients. Heart Rhythm, Apr. 2011, 592-598 : vol. 8, No. 4.
[NPL35] Wei, et. al., Fullerene-cryptand coated piezoelectric crystal urea sensor based on urease, Analytica Chimica Acta, 2001,77-85:437.
[NPL376] Gambro AK 96 Dialysis Machine Operators Manual, Dec. 2012. p. 1-140.
[NPL376] Gambro AK 96 Dialysis Machine Operators Manual, Dec. 2012. p. 141-280.
[NPL376] Gambro AK 96 Dialysis Machine Operators Manual, Dec. 2012. p. 281-420.
[NPL376] Gambro AK 96 Dialysis Machine Operators Manual, Dec. 2012. p. 421-534.
[NPL377] European Search Report 12819714.2-1651/2739325 PCT/US2012049398, dated Jun. 12, 2015.
[NPL378] PCT/US2014/14343 Intl Search Report & Written Opinion, dated May 9, 2014.
[NPL379] PCT/US2014/014350 International Search Report and Written Opinion dated May 2014.
[NPL37] U.S. Appl. No. 13/368,225 dated Feb. 7, 2012.
[NPL381] EP 14746791 Supplementary European Search Report dated Aug. 19, 2016.
[NPL382] EP 14746799 Supplementary European Seach Report dated Aug. 18, 2016.
[NPL383] Leifer et al., A Study on the Temperature Variation of Rise Velocity for Large Clean Bubbles, J. Atmospheric & Oceanic Tech., vol. 17, pp. 1392-1402, Oct. 2000.
[NPL384] Talaia, Terminal Velocity of a Bubble Rise in a Liquid Column, World Acad. of Sci., Engineering & Tech., vol. 28, pp. 264-68, Published Jan. 1, 2007.
[NPL386] The FHN Trial Group. In-Center. Hemodialysis Six Times per Week versus Three Times per Week, New England Journal of Medicine, 2010 Abstract.
[NPL39] PCT/US2012/034332, International Search Report, dated Jul. 5, 2012.
[NPL462] Office Action in U.S. Appl. No. 13/757,717 dated Dec. 26, 2014.
[NPL463] Office Action in U.S. Appl. No. 13/757,709 dated Jun. 6, 2015.
[NPL464] Office Action in U.S. Appl. No. 13/757,709 dated Jan. 7, 2016.
[NPL465] Office Action in U.S. Appl. No. 13/757,728 dated Jan. 8, 2016.
[NPL466] Office Action in U.S. Appl. No. 13/757,728 dated Aug. 12, 2016.
[NPL467] Office Action in U.S. Appl. No. 13/757,796 dated Apr. 13, 2015.
[NPL468] Office Action in U.S. Appl. No. 13/757,796 dated Dec. 21, 2015.
[NPL469] Office Action in U.S. Appl. No. 13/836,538 dated Aug. 19, 2015.
[NPL46] Siegenthaler, et al., Pulmonary fluid status monitoring with intrathoracic impedance, Journal of Clinical Monitoring and Computing, 24:449-451, published Jan. 12, 2011.
[NPL470] Office Action in U.S. Appl. No. 13/836,538 dated Jan. 11, 2016.
[NPL471] Office Action in U.S. Appl. No. 13/836,538 dated Apr. 27, 2016.
[NPL472] Office Action in U.S. Appl. No. 13/757,722 dated May 19, 2016.
[NPL473] Office Action in U.S. Appl. No. 13/757,709 dated Jan. 7, 2016.
[NPL474] Office Action in U.S. Appl. No. 13/757,693 dated Nov. 13, 2015.
[NPL475] Office Action in U.S. Appl. No. 13/757,693 dated May 23, 2016.
[NPL476] Office Action in U.S. Appl. No. 13/757,709 dated Jun. 6, 2015.
[NPL47] U.S. Appl. No. 61/480,544.
[NPL481] Office Action in U.S. Appl. No. 13/757,794 dated Oct. 21, 2015.
[NPL482] Office Action in U.S. Appl. No. 13/757,794 dated May 2, 2016.
[NPL483] Office Action in U.S. Appl. No. 13/424,525 dated Aug. 11, 2015.
[NPL484] Office Action in U.S. Appl. No. 13/424,525 dated Feb. 25, 2016.
[NPL485] Office Action in U.S. Appl. No. 13/424,525 dated Jun. 17, 2016.
[NPL486] Office Action in U.S. Appl. No. 13/424,525 dated Oct. 20, 2016.
[NPL487] Office Action in U.S. Appl. No. 13/424,479 dated Nov. 24, 2014.
[NPL488] Office Action in U.S. Appl. No. 14/566,686 dated Apr. 28, 2016.
[NPL489] Office Action in U.S. Appl. No. 13/424,533 dated Oct. 22, 2013.
[NPL490] Office Action in U.S. Appl. No. 13/424,533 dated Apr. 18, 2014.
[NPL491] Office Action in U.S. Appl. No. 13/424,533 dated Jan. 5, 2015.
[NPL492] Office Action in U.S. Appl. No. 13/424,533 dated Jun. 2, 2015.
[NPL493] Office Action in U.S. Appl. No. 13/424,533 dated Jul. 14, 2016.
[NPL496] Welgemoed, T.J., Capacitive Deionization Technology: An Alternative to desalination Solution, Desalination 183 (2005) 327-340.
[NPL497] European Search Report for App. No. 15193645.7, dated Apr. 15, 2016.
[NPL499] EP. App. 14746193.3 Search Report dated Oct. 19, 2016.
[NPL529] Office Action in U.S. Appl. No. 14/555,393 dated Nov. 1, 2016.
[NPL530] Office Action in U.S. Appl. No. 14/555,414 dated May 4, 2016.
[NPL531] Office Action in U.S. Appl. No. 14/555,414 dated Nov. 3, 2016.
[NPL534] Office Action in U.S. Appl. No. 13/586,824 dated Dec. 21, 2015.
[NPL535] Office Action in U.S. Appl. No. 13/586,824 dated Jun. 4, 2016.
[NPL546] Office Action in Chinese Application No. 201480007138.2 dated Sep. 28, 2016.
[NPL553] Ruperez et al., Comparison of a tubular pulsatile pump and a volumetric pump for continuous venovenous renal replacement therapy in a pediatric animal model, 51 ASAIO J. 372, 372-375 (2005).
[NPL554] St. Peter et al., Liver and kidney preservation by perfusion, 359 The Lancet 604, 606(2002).
[NPL555] Dasselaar et al., Measurement of relative blood volume changes during hemodialysis: merits and limitations, 20 Nephrol Dial Transpl. 2043, 2043-2044 (2005).
[NPL556] Ralph T. Yang, Adsorbents: Fundamentals and Applications 109 (2003).
[NPL557] Henny H. Billett, Hemoglobin and Hematocrit, in Clinical Methods: The History, Physical, and Laboratory Examinations 719(HK Walker, WD Hall, & JW Hurst ed., 1990).
[NPL558] Office Action in U.S. Appl. No. 13/565,733 dated Jan. 11, 2016.
[NPL559] Office Action in U.S. Appl. No. 13/565,733 dated Jun. 11, 2015.

(56) References Cited

OTHER PUBLICATIONS

[NPL55] U.S. Appl. No. 13/424,454.
[NPL560] Office Action in U.S. Appl. No. 13/586,824 dated Jun. 4, 2015.
[NPL561] Office Action in U.S. Appl. No. 13/757,792 dated Jun. 2, 2016.
[NPL562] Office Action in U.S. Appl. No. 13/757,796 dated Apr. 13, 2015.
[NPL563] Office Action in U.S. Appl. No. 13/757,796 dated Dec. 21, 2015.
[NPL564] Office Action in U.S. Appl. No. 13/835,735 dated Oct. 13, 2015.
[NPL565] Office Action in U.S. Appl. No. 13/836,079 dated Apr. 17, 2015.
[NPL566] Office Action in U.S. Appl. No. 13/836,079 dated Jun. 30, 2016.
[NPL569] Office Action in U.S. Appl. No. 13/791,755 dated Mar. 16, 2016.
[NPL570] Office Action in U.S. Appl. No. 13/791,755 dated Aug. 9, 2016.
[NPL571] Office Action in U.S. Appl. No. 13/835,735 dated Jun. 16, 2016.
[NPL572] Office Action in U.S. Appl. No. 13/836,079 dated Nov. 6, 2015.
[NPL578] Office Action in U.S. Appl. No. 13/791,755 dated Sep. 10, 2015.
[NPL579] Office Action in U.S. Appl. No. 13/791,755 dated Apr. 20, 2015.
[NPL57] U.S. Appl. No. 13/424,467.
[NPL580] Office Action in U.S. Appl. No. 14/259,589 dated Nov. 4, 2016.
[NPL581] Office Action in U.S. Appl. No. 14/261,651 dated Aug. 25, 2016.
[NPL586] International Search Report from International Application No. PCT/US2014/014347 dated May 9, 2014.
[NPL587] International Search Report for PCT/US2015/060090 date of completion is Feb. 9, 2016 (3 pages).
[NPL592] St. Peter et al., Liver and Kidney Preservation by perfusion, 369 The Lancet 604, 606 (2002).
[NPL593] Office Action for Chinese Application 20148007136.3, dated Jun. 2, 2016.
Extended European Search Report for App. No. 20160568.0, dated Jun. 17, 2020.
[NPL105] Brynda, et. al., The detection of toman 2-microglcbuiin by grating coupler immunosensor with three dimensional antibody networks. Biosensors & Bioelectronics, 1999, 363-368, 14(4).
[NPL10] Wheaton, et al., Dowex Ion Exchange Resins—Fundamentals of Ion Exchange; Jun. 2000, pp. 1-9. http://www.dow.com/scripts/litorder.asp?filepath=liquidseps/pdfs/noreg/177-01837.pdf.
[NPL111] Zhong, et. al., Miniature urea sensor based on H(+)-ion sensitive field effect transistor and its application in clinical analysis, Chin. J. Biotechnol., 1992, 57-65. 8(1).
[NPL119] PCT/US2012/034331, International Search Report and Written Opinion dated Jul. 9, 2012.
[NPL121] Roberts M, The regenerative dialysis (REDY) sorbent system. Nephrology, 1998, 275-278:4.
[NPL138] U.S. Appl. No. 61/480,544.
[NPL139] U.S. Appl. No. 61/480,541 dated Apr. 29, 2011.
[NPL142] Hemametrics, Crit-Line Hematocrit Accuracy, 2003, 1-5, vol. 1, Tech Note No. 11 (Rev. D).
[NPL144] Weissman, S., et al., Hydroxyurea-induced hepatitis in human immunodeficiency virus-positive patients. Clin. Infec. Dis, (Jul. 29, 1999): 223-224.
[NPL146] PCT/US2012/034334, International Search Report, dated Jul. 6, 2012.
[NPL147] PCT/US2012/034335, International Search Report, dated Sep. 5, 2012.
[NPL148] PCT/US/2012/034327, International Search Report, dated Aug. 13, 2013.
[NPL149] PCT/US/2012/034329, International Search Report, dated Dec. 3, 2012.
[NPL161] EP13182115.9-1651 European Search Report, dated Feb. 3, 2014.
[NPL162] International Search Report from PCT/US2012/051946 dated Mar. 4, 2013.
[NPL163] U.S. Appl. No. 61/526,209.
[NPL169] Wang, Fundamentals of intrathoracic impedance monitoring in heart failure, Am. J. Cardiology, 2007, 3G-10G: Suppl.
[NPL16] PCT/US2014/067650 International Search Report Written Opinion dated Mar. 9, 2015.
[NPL170] Bleyer, et al, Kidney International. Jun. 2006; 69(12):2268-2273.
[NPL172] U.S. Appl. No. 29/446,285, filed Feb. 1, 2013.
[NPL175] Marchant, et. al., In vivo Biocompatibility Studies 1: The Cage Implant System and a Biodegradable Hydrogel, J. Biomed. Mat. Res., 1983, 301-325: 17.
[NPL176] Bleyer, et. al., Sudden and cardiac death rated in hemodialysis patients, Kidney International. 1999, 1553-1559: 55.
[NPL178] PCT/US2012/025711, International Search Report dated Jul. 4, 2012.
[NPL179] PCT/US2013/020404, International Search Report, dated Jan. 4, 2013.
[NPL187] PCT/US2012/034333, International Preliminary Report on Patentability, dated Oct. 29, 2013.
[NPL188] PCT/US2012/034333, International Search Report, dated Aug. 29, 2012.
[NPL188] PCT/US2012/034333, International Search Report, dated Aug. 29, 2013.
[NPL189] PCT/US2012/051011, International Search Report, dated Jan. 17, 2014.
[NPL197] PCT/US2012/034330, International Preliminary Report on Patentability, dated Oct. 29, 2013.
[NPL205] Culleton, BF et al. Effect of Frequent Nocturnal Hemodialysis vs. Conventional Hemodialysis on Left Ventricular Mass and Quality of Life. 2007 Journal of the American Medical Association 298 (11), 1291-1299.
[NPL217] U.S. Appl. No. 13/757,722, filed Feb. 1, 2013.
[NPL218] U.S. Appl. No. 13/757,794, filed Feb. 2, 2012.
[NPL219] U.S. Appl. No. 13/791,755, filed Mar. 8, 2013.
[NPL21] U.S. Appl. No. 13/424,479 dated Nov. 1, 2012.
[NPL220] U.S. Appl. No. 13/757,792, filed Feb. 2, 2013.
[NPL222] U.S. Appl. No. 13/757,794, filed Feb. 2, 2013.
[NPL227] U.S. Appl. No. 13/837,287, filed Mar. 15, 2013.
[NPL22] U.S. Appl. No. 13/424,429 dated Nov. 1, 2012.
[NPL230] Redfield, et. al, Restoration of renal response to atria! natriuretic factor in experimental low-output heat failure, Am. J. Physiol., Oct. 1, 1989, R917-923:257.
[NPL231] Rogoza, et. al., Validation of A&D UA-767 device for the self-measurement of blood pressure, Blood Pressure Monitoring, 2000, 227-231, 5(4).
[NPL234] Lima, et. al., An electrochemical sensor based on nanostructure hollsndite-type manganese oxide for detection of potassium ion, Sensors, Aug. 24, 2009, 6613-8625, 9.
[NPL235] Maclean, et, al., Effects of hindlimb contraction on pressor and muscle interstitial metabolite responses in the cat, J. App. Physiol., 1998, 1583-1592, 85(4).
[NPL237] U.S. Appl. No. 13/757,693, dated Feb. 1, 2013.
[NPL238] PCT Application, PCT/US20013/020404, filed Jan. 4, 2013.
[NPL23] U.S. Appl. No. 13/424,525.
[NPL240] U.S. Appl. No. 13/836,973, filed Mar. 15, 2013.
[NPL241] U.S. Appl. No. 14/259,655, filed Apr. 23, 2014.
[NPL242] U.S. Appl. No. 14/259,589, filed Apr. 23, 2014.
[NPL243] U.S. Appl. No. 13/757,693, filed Jan. 4, 2013.
[NPL244] U.S. Appl. No. 13/836,079, filed Mar. 15, 2013.
[NPL245] U.S. Appl. No. 14/240,129, filed Aug. 22, 2013.
[NPL247] U.S. Appl. No. 13/835,735, filed Mar. 15, 2013.
[NPL248] PCT/US2014/014345 International Search Report and Written Opinion, dated May 2014.
[NPL250] U.S. Appl. No. 13/835,735 IDS, filed Jun. 13, 2013.
[NPL594] Office Action for Chinese Application 20148007136.3, dated Jan. 26, 2017.

(56) References Cited

OTHER PUBLICATIONS

[NPL597] Franks, Gene, Cabon Filtration: What it does, What it doesnt, Mar. 14, 2012, pp. 1-3.
[NPL597] Franks, Gene, Carbon Filtration: What it does, What it doesnt, Mar. 14, 2012, pp. 1-3.
[NPL599] PCT/US2014/014352 International Prelminary Report on Patentability, dated Aug. 14, 2015.
[NPL600] Hamm et al,. Sorbent regenerative hemodialysis as a potential cuase of acute hypercapnia, Kidney International, vol. 21, (1982), pp. 416-418.
[NPL624] Office Action in Chinese Application No. 201480007132.5 dated Jul. 19, 2017.
[NPL627] EP Search Report for Application No. 16204175.0 dated Mar. 29, 2017.
[NPL629] Office Action for Chinese Application 201510713880.1 dated Apr. 1, 2017.
[NPL62] U.S. Appl. No. 13/424,533.
[NPL631] Understanding Dialysate Bicarbonate—A simple approach to understanding a complex equation by Fresenius Medical Care, 2011.
[NPL635] International Search Report, Application PCT/US2016/043948, dated Feb. 2, 2017.
[NPL636] Written Opinion, Application PCT/2016/043948, dated Feb. 2, 2017.
[NPL637] International Search Report, Application PCT/US2016/043935, dated Feb. 2, 2017.
[NPL638] Written Opinion, Application PCT/US2016/043935, dated Feb. 2, 2017.
[NPL639] International Search Report and Written Opinion in App. No. PCT/US2012/049398 dated Feb. 25, 2013.
[NPL641] PCT/US2014/014343 Written Opinion dated Jan. 2, 2015.
[NPL642] PCT/US2014/014343 International Preliminary Search Report dated Mar. 18, 2015.
[NPL643] European Search Report for EP Appl. No. 1474679.4 dated Aug. 19, 2016.
[NPL644] Office Action for Chinese Application 201510761050.6 dated Aug. 2, 2017.
[NPL645] PCT/US2014/014355 International Search Report and Written Opinion dated May 1, 2014.
[NPL646] PCT/US2014/014355 International Preliminary Report dated Apr. 13, 2015.
[NPL647] EP 14746817.7 European Search Report dated Sep. 27, 2016.
[NPL650] Office Action in Chinese Application No. 201480007132.5 dated Feb. 27, 2017.
[NPL652] Office Action in Chinese Application No. 201280047921.2 dated Jun. 11, 2015.
[NPL654] International Preliminary Report from International Application No. PCT/US2014/014348 dated Jan. 9, 2015.
[NPL655] European Search Report from European Application No. EP 14746193.3 dated Oct. 19, 2016.
[NPL656] European Search Report from European Application No. EP 14746193.3 dated Jun. 8, 2016.
[NPL661] PCT/US2014/014346 Writtent Opinion dated Apr. 10, 2015.
[NPL662] PCT/US2014/014346 International Search Report and Writtent Opinion dated May 23, 2014.
[NPL663] EP 14746415.0 European Search Report dated Aug. 22, 2016.
[NPL664] Office Action in European Application No. EP 14746415.0 dated Apr. 19, 2017.
[NPL665] PCT/US2014/014357 International Search Report and Written Opinion dated May 19, 2014.
[NPL666] PCT/US2014/014357 Written Opinion dated Feb. 18, 2015.
[NPL667] European Search Report in European Application No. EP 14746010.9 dated Sep. 15, 2016.
[NPL670] Office Action in European Application No. 14746415.0 dated Apr. 19, 2017.
[NPL67] U.S. Appl. No. 13/424,490.
[NPL68] U.S. Appl. No. 13/424,517.
[NPL704] Written Opinion for PCT/US2015/060090 dated Feb. 16, 2016.
[NPL705] EP 13733819 Supplementary European Search Report dated Jan. 28, 2015.
[NPL713] EP Search Report and Opinion for Application No. 15193720.8 dated May 2, 2016.
[NPL714] Office action for European Application No. 15193720.8 dated Apr. 25, 2017.
[NPL723] PCT/US2012/051011, International Search Report and Written Opinion, dated Mar. 4, 2013.
[NPL724] Office Action for European Application No. 14746611.4 dated Jan. 3, 2017.
[NPL725] Supplemental Search Report and Search Opinion for European Application No. 14746611.4 dated Aug. 18, 2016.
[NPL729] Office Action in Chinese Application No. 201480007138.2 dated May 31, 2017.
[NPL739] European Office Action in Application No. 14746793.0 dated Apr. 13, 2017.
[NPL743] Examination report in Australian Application No. 2014212141 dated May 26, 2017.
[NPL744] Examination report for Australian Application 2015361083 dated Jul. 20, 2017.
[NPL750] European Search Report and Search Opinion for European Application EP15193720 dated May 2, 2016.
[NPL752] International Preliminary Report on Patentability for PCT2015/060090 dated Jun. 13, 2017.
[NPL753] European Search Report for European Application EP 15193830.5 dated May 4, 2016.
[NPL754] Office Action for European Application No. 15193645.7 dated Apr. 21, 2017.
[NPL81] U.S. Appl. No. 61/480,539 dated Apr. 29, 2011.
[NPL84] U.S. Appl. No. 61/480,535 dated Apr. 29, 2011.
[NPL90] Nedelkov, et. al., Design of buffer exchange surfaces and sensor chips for biosensor chip mass spectrometry, Proteomics, 2002, 441-446, 2(4).
PCT/US2017/025868 International Search Report dated Jun. 29, 2017.
PCTUS2017025858 International Search Report dated Jun. 29, 2017.
PCTUS2017025858 Written Opinion dated Jun. 29, 2017.
PCTUS2017025876 International Search Report dated Jun. 29, 2017.
PCTUS2017025876 Written Opinion dated Jun. 29, 2017.
Office Action in European App. No. 19158804.5, dated Sep. 4, 2020.

\* cited by examiner

SORBENT MANIFOLD FOR A DIALYSIS SYSTEM

CROSS-REFERENCE TO RELATED APPLICATION

This application claims the benefit of and priority to U.S. Provisional Patent Application No. 62/625,540 filed Feb. 2, 2018, the entire disclosure of which is incorporated by reference herein.

FIELD OF THE INVENTION

The present invention relates to a sorbent manifold and includes related systems and methods having a plurality of passageways fluidly connectable to one or more valves and one or more sensors and components for use in a sorbent dialysis system. The sorbent manifold can control the one or more valves to direct fluid to either pass through a sorbent cartridge or bypass the sorbent cartridge based on measurements obtained from sensors.

BACKGROUND

A sorbent dialysis system uses a sorbent cartridge containing one or more sorbent materials to remove impurities from dialysate in the dialysis system. Prior to treatment, the dialysis system can be primed wherein priming fluid does not need to pass through the sorbent cartridge. However, known systems fail to control priming fluid, and cannot selectively bypass specific components such as a sorbent cartridge under proper control. The lack of control often results in fluid being wasted or extra time being required to complete a priming operation. During treatment, fluid such as dialysate should be directed away from the sorbent cartridge under harmful circumstances, for example, when a sorbent cartridge's capacity to adsorb ammonia approaches "ammonia breakthrough," or when the dialysate is pressurized to a level exceeding a desired range. Known systems fail to control dialysate flow and cannot selectively pass a fluid through the sorbent cartridge or cannot control the flow of fluid to a drain prior to reaching a component in the device, such as a sorbent cartridge.

Conventional dialysis machines oftentimes contain complex tubing that result in a device that may be too complicated to be serviced in a home dialysis setting or by non-professionally trained personnel. Complicated tubing snaking through conventional machines form many different fluid pathways making servicing difficult. The known tubing systems also take up more volume and can result in larger than necessary compartment spaces inside conventional machines. The snaking tubes are prone to kinking, leakage, or damage. The complicated tubing systems impose a design burden, increase manufacturing costs, and can make installation and servicing difficult or prohibitive. As such, conventional dialysis treatments relying on complex tubing are often restricted to clinics, hospitals, and managed dialysis centers where they can be properly serviced and managed.

One example of a known system is U.S. Pat. No. 8,137,553 ("Fulkerson"), which uses a plastic molded manifold to support blood and dialysate fluid pathways along with sensors, valves, and pumps. Fulkerson is directed to a disposable manifold that can be switched between a priming mode and a treatment mode of operation. The manifold in Fulkerson uses a two-way valve in the manifold to direct the dialysate flow through the blood circuit to prime the circuit for use in treatment. However, Fulkerson and similar known devices cannot divert fluids to selectively pass through a sorbent cartridge based on one or more fluid characteristics of the dialysate, such as pressure and conductivity, measured by one or more sensors on a dialysate flow path. Fulkerson also cannot divert fluids to avoid passing around a sorbent cartridge when ammonia breakthrough occurs during dialysis. Known systems and methods either fail to actively control a fluid direction in a dialysis system or fail to effectively control diverting fluid in a sorbent-based dialysis system.

Hence, there is a need for a manifold and related integrated systems and methods that can actively control fluid directions during priming and treatment modes of operation in a sorbent dialysis system. There is a need for a manifold and integrated systems and methods that can provide effective control to divert a fluid flow into a sorbent cartridge to obtain purified dialysate in a controlled manner in a dialysis system. To increase manufacturability and reduce costs, there is a further need for components, systems, and methods that can use a manifold containing valves capable of controlling a fluid direction to either bypass or flow through a sorbent cartridge, rather than relying upon one or more separate sets of tubing. In a manifold, there is a need for tubing and functional components, such as valves and sensors, that can be integrated into one or more parts, which can be assembled together to form a compact structure for operation in a dialysis system. There is a need for such an integrated manifold to exert an effective control on a sorbent dialysis system.

SUMMARY OF THE INVENTION

The first aspect of the invention relates to a sorbent manifold. In any embodiment, the sorbent manifold can comprise a plurality of passageways fluidly connectable to a sorbent dialysis system, one or more valves and one or more sensors, the one or more valves directing fluid to either pass through a sorbent cartridge in the sorbent dialysis system or bypass the sorbent cartridge based on measurements of the one or more sensors, and at least one sorbent inlet fluidly connectable to an outlet of the sorbent cartridge.

In any embodiment, the sorbent manifold can comprise a first valve fluidly connecting a first passageway to a second passageway, the first passageway fluidly connectable to a first inlet of the sorbent manifold and the second passageway fluidly connectable to a first outlet of the sorbent manifold, the first outlet of the sorbent manifold fluidly connectable to an inlet of the sorbent cartridge; and a second valve fluidly connecting a third passageway to a fourth passageway, the third passageway fluidly connectable to a second outlet of the sorbent manifold and the fourth passageway fluidly connectable to the at least one sorbent inlet of the sorbent manifold, the at least one sorbent inlet of the sorbent manifold fluidly connectable to the outlet of the sorbent cartridge.

In any embodiment, the sorbent manifold can comprise the one or more sensors selected from a group consisting of an ammonia sensor, a temperature sensor, a conductivity sensor, and a pressure sensor.

The second aspect of the invention relates to a sorbent manifold system. In any embodiment, the sorbent manifold system can comprise a plurality of passageways fluidly connectable to a sorbent dialysis system, one or more valves and one or more sensors, a controller controlling the one or more valves to direct fluid to either pass through a sorbent cartridge in the sorbent dialysis system or bypass the sorbent cartridge based on measurements of the one or more sensors, and at least one sorbent inlet fluidly connectable to an outlet of the sorbent cartridge, wherein the controller controls the fluid to enter the at least one sorbent inlet from the outlet of the sorbent cartridge.

In any embodiment, the sorbent manifold system can comprise the controller in communication with the first valve and the second valve; the controller controlling the first valve and second valve to direct the fluid from one of the first inlet and the at least one sorbent inlet to one of the first outlet and the second outlet.

In any embodiment, the controller is programmed to selectively direct the fluid from the first inlet to either the first outlet or second outlet based on data from the one or more sensors.

In any embodiment, the sorbent manifold system can comprise the at least one sensor including a pressure sensor; and wherein the controller selectively directs fluid from the first inlet to the second outlet if a pressure is above a predetermined range. In one embodiment, the predetermined range can be a pressure equal to or greater than about 2,500 mmHg.

In any embodiment, the sorbent manifold system can comprise the controller in communication with an ammonia sensor downstream of the sorbent cartridge, and wherein the controller selectively directs fluid from the first inlet to the second outlet if ammonia is detected by the ammonia sensor.

In any embodiment, the controller controls the first valve and second valve to direct the fluid from the first inlet to the first outlet and from the at least one sorbent inlet to the second outlet.

In any embodiment, the first outlet is fluidly connectable to a drain valve prior to reaching the sorbent cartridge inlet, the drain valve selectively directing fluid to the sorbent cartridge inlet or to a drain line.

In any embodiment, the drain valve can be positioned in a separate drain manifold.

In any embodiment, the sorbent manifold can comprise the first outlet and the second inlet fluidly connectable to each other through the sorbent cartridge inlet and outlet.

In any embodiment, the first valve and second valve can be configured to selectively direct fluid from the first inlet to the first outlet and from the second inlet to the second outlet in a treatment mode.

In any embodiment, the first valve and second valve can be configured to selectively direct the fluid from the first inlet to the second outlet in a sorbent bypass mode.

The features disclosed as being part of the first aspect of the invention can be in the first aspect of the invention, either alone or in combination.

The third aspect of the invention relates to a method having the steps of pumping a dialysate from a dialyzer outlet, through a dialysate flow path to the first inlet of the sorbent manifold, pumping the dialysate through the first passageway and second passageway to the first outlet of the sorbent manifold, pumping the dialysate from the first outlet of the sorbent manifold to an inlet of the sorbent cartridge, pumping the dialysate from an outlet of the sorbent cartridge to the second inlet of the sorbent manifold, pumping the dialysate from the second inlet to the second outlet of the sorbent manifold and into the dialysate flow path downstream of the sorbent cartridge, and pumping the dialysate to a dialyzer inlet.

In any embodiment, the method can comprise the steps of measuring an ammonia concentration in the dialysate downstream of the sorbent cartridge; and switching the first valve and second valve to pump fluid from the first inlet to the second outlet in response to ammonia in the dialysate.

In any embodiment, the step of switching the first valve and second valve in response to ammonia in the dialysate can be performed by the controller in communication with an ammonia sensor downstream of the sorbent cartridge.

In any embodiment, the method can comprise the step of generating an alert if ammonia is measured in the dialysate.

In any embodiment, the method can comprise the steps of measuring a pressure in the dialysate in the first passageway; and switching the first valve and second valve to pump the fluid from the first inlet to the second outlet of the sorbent manifold in response to a pressure of over a predetermined range.

In one embodiment, the predetermined range can be a pressure equal to or greater than about 2,500 mmHg.

In any embodiment, the step of switching the first valve and second valve in response to the pressure in the dialysate is performed by the controller in communication with a pressure sensor in the first passageway.

In any embodiment, the method can comprise the step of generating an alert if the pressure in the first passageway exceeds a predetermined range.

In one embodiment, the predetermined range can be a pressure in the first passageway equal to or greater than about 2,500 mmHg.

The features disclosed as being part of the second aspect of the invention can be in the second aspect of the invention, either alone or in combination.

BRIEF DESCRIPTION OF THE DRAWINGS

FIG. 2D is a perspective view of a dialysate flow path including a sorbent manifold.

DETAILED DESCRIPTION OF THE INVENTION

Figure 1:
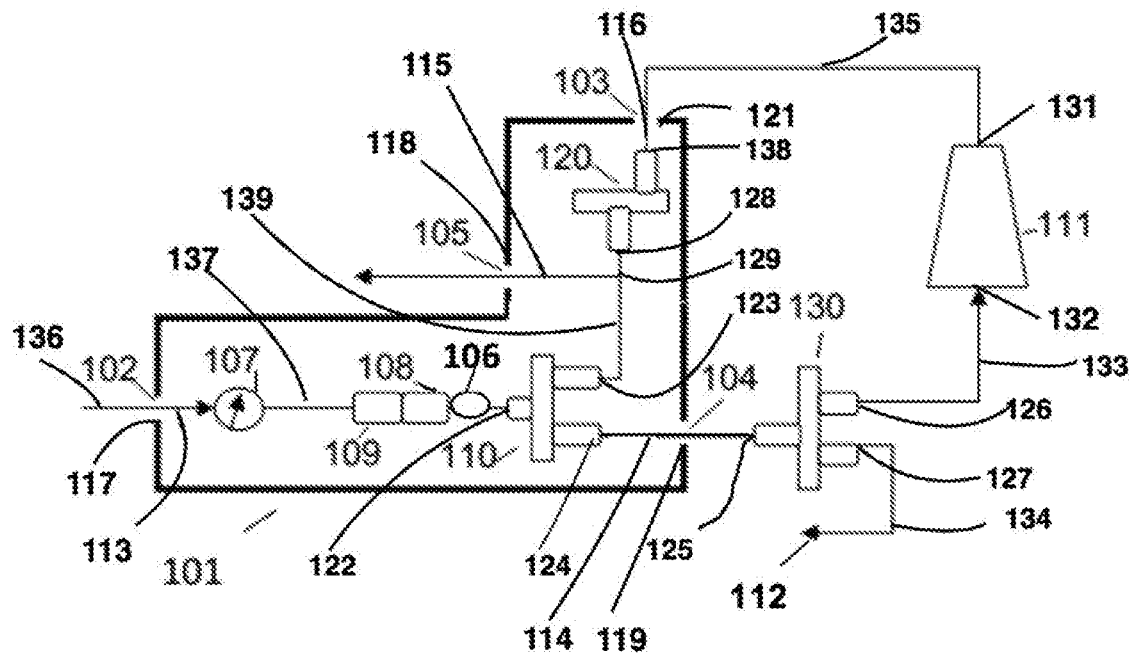
FIG. 1 is a portion of a dialysate flow path including a sorbent manifold.

Unless defined otherwise, all technical and scientific terms used generally have the same meaning as commonly understood by one of ordinary skill in the art.

The articles "a" and "an" are used to refer to one or to over one (i.e., to at least one) of the grammatical object of the article. For example, "an element" means one element or over one element.

The term "ammonia concentration" or "ammonia level" refers to a total concentration of ammonia and/ammonium ions in a fluid, gas, or combinations thereof.

The term "ammonia is detected" can refer to an ammonia concentration or level that exceeds a minimum detectable level of ammonia. In one embodiment, the ammonia can be detected by a sensor.

The term "ammonia sensor" refers to a device that performs all or part of a function to detect a level of, or measure a concentration of, ammonia and/or ammonium ions in a fluid, gas, or combinations thereof.

The term "bypass" refers to a flow path wherein a fluid, gas, or combinations thereof can pass around a certain component positioned in the flow path. For example, a sorbent cartridge can be bypassed such that fluid can avoid flowing through the sorbent cartridge and continue in the flow path.

The term "comprising" includes, but is not limited to, whatever follows the word "comprising." Use of the term indicates the listed elements are required or mandatory but that other elements are optional and may be present.

The term "communication" or "electronic communication" refers to any transfer of signs, signals, images, sounds, or data in whole or in part between two or more components by suitable means, such as by a wire, wirelessly, or a combination of both. Any method, component, device, or means known in the art can be used for the communication. Electronic communication can occur between a controller and a sensor and/or valve.

A "conductivity sensor" is a device for measuring the electrical conductance of a solution and/or the ion, such as a sodium ion, concentration of a solution.

The term "consisting of" includes and is limited to whatever follows the phrase "consisting of" The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

A "controller" can refer to a device which monitors and affects the operational conditions of a given system, component, or device. The operational conditions are typically referred to as output variables of the system wherein the output variables can be affected by adjusting certain input variables.

The terms "control," "controlling," or "controls" can refer to the ability of one component to direct the actions of a second component.

A "control system" can be a combination of components acting together to maintain a system to a desired set of performance specifications. The control system can use processors, memory and computer components configured to interoperate to maintain the desired performance specifications. The control system can also include fluid or gas control components, and solute control components as known within the art to maintain the performance specifications.

The term "data from the one or more sensors" broadly refers to any data obtained or derived from the measurements obtained from the one or more sensors. or any information related to the one or more sensors.

The term "dialysate" describes a fluid into or out of which solutes from a fluid to be dialyzed diffuse through a membrane. An initial dialysate used for therapy typically contains electrolytes close in concentration to the physiological concentration of electrolytes found in blood. However, the concentration of the dialysate can change over the course of therapy, and can further be adjusted as desired.

The term "dialysate flow path" can refer to a fluid pathway or passageway that conveys a fluid, such as dialysate and is configured to form at least part of a fluid circuit for peritoneal dialysis, hemodialysis, hemofiltration, hemodiafiltration or ultrafiltration.

The term "dialyzer" refers to a cartridge or container with two flow paths separated by semi-permeable membranes. One flow path is for blood and one flow path is for dialysate. The term "dialyzer" can refer to a cartridge or container with two flow paths separated by semi-permeable membranes. One flow path is for blood and one flow path is for dialysate. The membranes can be in hollow fibers, flat sheets, or spiral wound or other conventional forms known to those of skill in the art. Membranes can be selected from any one or combination of materials: polysulfone, polyethersulfone, poly (methyl methacrylate), modified cellulose, or other materials known to those skilled in the art. The membranes can be in hollow fibers, flat sheets, or spiral wound or other conventional forms known to those of skill in the art. Membranes can be selected from any one or combination of materials: polysulfone, polyethersulfone, poly (methyl methacrylate), modified cellulose, or other materials known to those skilled in the art The term "dialyzer inlet" refers to an inlet of a dialyzer for fluid to enter the dialyzer. The term "dialyzer outlet" refers to an outlet of the dialyzer for fluid to leave the dialyzer.

The term "direct fluid" refers to an action during which a fluid is forced to flow towards a particular direction along a predetermined flow path. Directing fluid can be controlled by one or more valves that can be set in opened or closed positions for particular flow directions of the fluid passing through the valves. The term "selectively direct" refers to a fluid being directed to at least one particular direction out of two or more possible directions that the fluid can be directed.

The term "drain valve" refers to a valve that can direct the flow of fluid by opening, closing or obstructing one or more pathways to allow the fluid to flow into a drain.

The term "drainline" or "drain line" refers to a fluid line or gas line through which a fluid, gas, or combinations thereof can flow into a drain.

The term "drain manifold" refers to a component containing one or more fluid passageways and one or more components such as valves and sensors, where one or more valves are controlled by a controller based on measurements of the one or more sensors to direct fluid to either flow into a drain or pass around the drain. The drain manifold can be used as part of the dialysis system. The drain manifold can be combined with one or more other components of the dialysis system, such as a sorbent manifold, to form one integrated structure.

The term "downstream" refers to a position of a first component in a flow path relative to a second component wherein fluid, gas, or combination thereof, can pass by the second component prior to the first component during normal operation. The first component can be said to be "downstream" of the second component, while the second component is "upstream" of the first component.

The term "fluid" can be any substance without a fixed shape that yields easily to external pressure such as a gas or a liquid. Specifically, the fluid can be water containing any solutes at any concentration. The fluid can also be dialysate of any type including fresh, partially used, or spent. The fluid can also contain one or more dissolved gas.

The term "fluidly connectable" refers to the ability to provide passage of fluid, gas, or combinations thereof, from one point to another point. The ability to provide such passage can be any mechanical connection, fastening, or forming between two points to permit the flow of fluid, gas, or combinations thereof. The two points can be within or between any one or more of compartments, modules, systems, components, and rechargers, all of any type.

The term "fluidly connected" refers to a particular state or configuration of one or more components such that fluid, gas, or combination thereof, can flow from one point to another point. The connection state can also include an optional unconnected state or configuration, such that the two points are disconnected from each other to discontinue flow. It will be further understood that the two "fluidly connectable" points, as defined above, can from a "fluidly connected" state. The two points can be within or between any one or more of compartments, modules, systems, components, and rechargers, all of any type.

A "fluid line" can refer to a tubing or conduit through which a fluid, gas, or fluid containing gas can pass. The fluid line can also contain gas during different modes of operation such as cleaning or purging of a line.

The term "generating an alert" or to "generate an alert" can refer to generating or signaling to a user a state or condition of a system. The term "alert" refers to any sign, text, voice, video, image or any indication of a state or a condition of a system. An alert can be given based on measurements of a sensor, for instances, when a pressure level of fluid exceeds a predetermined range, or an ammonia is detected in the fluid.

The term "inlet" can refer to a portion of a component through which fluid and/or gas can be drawn into the component. In one non-limiting example, the component can be a manifold.

The term "in response to" refers to an action of responding to a condition, the condition can be a measurement by a sensor, a signal transferred between two components, or an operating status of a component, such as open or close status of a valve. The term "in response to" can mean "based on" or "according to." A controller can react to certain signals received from a component positioned in another component or device, such as a sorbent manifold. Further, components in a sorbent manifold can react "in response to" signals sent from a controller.

The term "measuring" or "to measure" can refer to determining any parameter or variable. The parameter or variable can relate to any state or value of a system, component, fluid, gas, or mixtures of one or more gases or fluids.

The term "measurement" refers to data or information of the parameter or variable determined. The term "according to measurements" refers to further calculation or operation that is proceeded based on or depending on the measurements.

The term "outlet" refers to a portion of a component through which fluid or gas can be pulled out of the component in a fluid line, conduit, or fluid passageway of any type. In one non-limiting embodiment, the component can be a manifold.

The term "passageway" refers to a fluid path through which fluid or gas can flow from one location to another location, where the passageway has walls to restrain the fluid or gas within the passageway and the walls at least in-part surround the fluid or gas and connect the two locations.

The term "pass through" refers to an action of fluid or gas passing a component positioned in a flow path. The fluid or gas can enter an inlet of the component and exit via an outlet of the component to continue the flow path.

The term "perform" refers to a component, processor, algorithm, or method carrying out one or more actions. The term "performed" refers to one or more actions that are carried out by the component, processor, algorithm, or method.

The actions can be set by instructions implemented by a component, processor, algorithm, or method of any type.

The term "predetermined range" or "desired range" is any range of possible values for a parameter obtained in advance or a priori to actual use in a method.

The term "pressure" refers to a force exerted by a gas on the walls of a component, container, or conduit.

The term "pressure sensor" can refer to a device or any suitable component for measuring the pressure of a gas or fluid in a vessel, container, or fluid line.

The term "programmed," when referring to a controller, can mean a series of instructions that cause a controller to perform certain steps.

The term "pump" refers to any device that causes the movement of fluids or gases by applying suction or pressure.

The terms "pumping dialysate" or to "pump dialysate" refer to moving dialysate through a flow path with a pump.

"Purified water" can be defined as water produced by distillation, deionization, reverse osmosis, or other suitable processes and that meets the definition of "purified water" in the United States Pharmacopeia, 23d Revision, Jan. 1, 1995, and the FDA at 21 CFR Section § 165.110(a)(2)(iv). Other criteria for purified water can be determined by those of skill in the art, particularly as relating to purified water suitable for dialysis.

The term "selecting" or to "select" refers to choosing a variable or parameter from a set of possible variables or parameter.

The term "selectively directing" refers to directing a fluid or gas to flow in at least one particular direction.

The term "sensor" refers to a device, module, or system that can detect events or changes in its environment and indicate the information or send the information to other electronics, often a computer processor. The environment can be a fluid, gas, or a combination of fluid and gas. A sensor may detect changes of one or more fluid characteristics such as ammonia level, pressure, conductivity, and temperature.

The term "sorbent cartridge" refers to a cartridge containing one or more sorbent materials for removing specific solutes from solution, such as urea. The term "sorbent cartridge" does not require the contents in the cartridge to be sorbent based, and the contents of the sorbent cartridge can be any contents that can remove waste products from a dialysate. The sorbent cartridge may include any suitable amount of one or more sorbent materials. In certain instances, the term "sorbent cartridge" can refer to a cartridge which includes one or more sorbent materials in addition to one or more other materials capable of removing waste products from a fluid such as dialysate. The term "sorbent cartridge" can also include configurations where at least one material in the cartridge does not act by mechanism of adsorption or absorption.

The term "sorbent dialysis system" refers to a dialysis system containing one or more sorbent cartridges for removing impurities from fluid passing through the sorbent cartridges. The sorbent dialysis system can be used for regeneration of spent dialysate or obtaining purified water.

The term "sorbent inlet" refers to an inlet of a component, such as a sorbent manifold, which can be fluidly connected to a dialysis flow system. The sorbent inlet can be fluidly connectable to an outlet of a sorbent cartridge in the dialysis flow system.

The term "sorbent line" refers to a fluid line that can connect to an inlet of a sorbent manifold and an outlet of a sorbent cartridge in a dialysis system.

The term "sorbent manifold" refers to a component containing one or more fluid passageways and one or more components such as valves and sensors, where a controller can control one or more valves based on measurements of the one or more sensors to direct fluid to either pass through or bypass a sorbent cartridge in a dialysis system. The sorbent manifold can be used as part of the dialysis system.

The term "sorbent bypass mode" refers to a sorbent manifold operating to selectively direct fluid that passes through the sorbent manifold to bypass a sorbent cartridge by controlling one or more valves based on measurements of one or more sensors in the sorbent manifold, the sorbent cartridge fluidly connectable to the sorbent manifold in a dialysis system.

The term "system drain mode" refers to a sorbent manifold operating to drain fluid in a fluid line or passageway between a first valve and a second valve by controlling intermittently the first and second valve to selectively direct the fluid to flow away from the fluid line towards an outlet of the sorbent manifold.

The term "switching a valve" refers to change the from a first position to a second position so that a fluid can be directed to a direction defined by the second position from a direction defined by the first position. The first position and second position of a valve can be an opened position and a closed position.

A "temperature sensor" is a sensor capable of determining the temperature of a fluid, gas, or combination thereof.

The term "treatment mode" refers to a sorbent manifold operating to selectively direct fluid exiting the sorbent manifold to pass through a sorbent cartridge positioned downstream to the sorbent manifold in a flow path to continue the flow path. The fluid can be dialysate in a dialysate flow path.

"Urease" is an enzyme that catalyzes the conversion of urea into carbon dioxide and ammonium ions.

The term "upstream" refers to a position of a first component in a flow path relative to a second component wherein fluid, gas, or combinations thereof, will pass by the first component prior to the second component during normal operation. The first component can be said to be "upstream" of the second component, while the second component is "downstream" of the first component.

A "valve" can be a device capable of directing the flow of fluid or gas by opening, closing or obstructing one or more pathways to allow the fluid or gas to travel in a path. One or more valves configured to accomplish a desired flow can be configured into a "valve assembly."

Sorbent Manifold

The sorbent manifolds of the invention can be used in integrated systems and methods for use in dialysis having one or more components such as valves and sensors and fluid passageways to direct fluid or gas to flow through a selective passageway from one location to another location within the sorbent manifold. The fluid or gas can be forced to enter and exit the sorbent manifold following one or more designated passageways. The compact structure of the sorbent manifold avoids the need of complex tubing and can result in an enhanced and efficient control of fluid flow. Using a manifold can also make the dialysis system more compact and portable resulting in a dialysis machine that takes up less space and is easier to handle. The dialysis system containing a sorbent manifold also assists a patient or a non-professional technician to service the machine without the need for involved and sophisticated training. The sorbent manifolds can be made of plastic using well-known techniques, and thus reduce overall manufacturing cost.

FIG. 1 is a portion of a dialysate flow path including a sorbent manifold 101 in a sorbent dialysis system. A dialysate flow path is a fluid pathway or passageway that conveys a fluid, such as dialysate and is configured to form at least part of a fluid circuit for peritoneal dialysis, hemodialysis, hemofiltration, hemodiafiltration or ultrafiltration. The sorbent manifold 101 can be fluidly connected to the dialysate flow path at a position upstream of a sorbent cartridge 111, wherein fluid, gas, or combinations thereof, can bypass the sorbent manifold 101 prior to the sorbent cartridge 111 during dialysis. In other words, the sorbent cartridge 111 can be positioned at a position downstream of the sorbent manifold 101. The sorbent cartridge 111 can be a cartridge containing one or more sorbent materials for removing specific solutes from solution, such as urea. The dialysis system containing one or more sorbent cartridges for removing impurities from fluid passing through the sorbent cartridges can be used for regenerating spent dialysate or obtaining purified water.

The sorbent manifold 101 can selectively direct fluid to either pass through or bypass the sorbent cartridge 111. The sorbent manifold 101 can direct a fluid or gas entering the sorbent manifold 101 to selectively flow through one or more direction towards a specified outlet of the sorbent manifold 101. For instance, spent dialysate can pass around the sorbent cartridge 111 to continue the flow path. The fluid or gas can also enter an inlet 132 of the sorbent cartridge 111, pass through one or more sorbent materials in the sorbent cartridge 111, and exit via an outlet 131 of the sorbent cartridge 111 to continue the flow path. The sorbent cartridge 111 can be used to obtain purified water. "Purified water" can be defined as water produced by distillation, deionization, reverse osmosis, or other suitable processes and that meets the definition of "purified water" in the United States Pharmacopeia, 23d Revision, Jan. 1, 1995, and the FDA at 21 CFR Section § 165.110(a)(2)(iv). Other criteria for purified water can be determined by those of skill in the art, particularly as relating to purified water suitable for dialysis.

The sorbent manifold 101 can comprise a plurality of passageways fluidly connectable to one or more valves and one or more sensors in a sorbent dialysis system, wherein the sorbent manifold 101 controls the one or more valves to direct fluid to either pass through a sorbent cartridge 111 in the sorbent dialysis system or bypass the sorbent cartridge 111 based on measurements obtained from one or more sensors. The sorbent manifold 101 can direct an action in one or more valves to direct fluid by controlling the one or more valves in an opened or closed position.

The sorbent manifold 101 can include components such as valves and sensors positioned to one or more of a first, second, and third parts. The valve can direct the flow of fluid or gas by opening, closing or obstructing one or more pathways to allow the fluid or gas to travel in a specified flow path. One or more valves configured to accomplish a desired flow can be configured into a valve assembly. The sensor can be any device, module, or system of components that can be used to detect events or changes in the sorbent manifold and send the information to other electronics, such as a computer processor or specific purpose computer. The sensor can detect changes of one or more fluid characteristics such as ammonia level, pressure, conductivity, and temperature.

The valves and sensors can also be removable when the first, second, and third parts are disassembled. The sorbent manifold 101 can be formed from any suitable material such as plastic, metal, or composites. The sorbent manifold 101 can be fluidly connected to the dialysate flow path through ports or connectors attached to one or more of the first, second, and third parts.

The sorbent cartridge 111 can include one or more layers of sorbent materials. The sorbent cartridge 111 can include aluminum oxide for removal of fluoride and heavy metals, activated carbon that operates to adsorb non-ionic molecules, organic molecules, and chlorine from the water, along with some endotoxins or bacterial contaminants. The sorbent cartridge 111 can also include other components that work primarily by physical and chemical adsorption, combined with one or more ion exchange materials. The sorbent cartridge 111 can contain urease, which catalyzes the conversion of urea to ammonium ions and carbon dioxide. The sorbent cartridge 111 can additionally include a microbial filter and/or a particulate filter. A microbial filter can further reduce an amount of bacterial contaminants present in the fluid. The sorbent cartridge 111 can be used to obtain regenerated dialysate from the spent dialysate for reuse in the dialysis system. The sorbent cartridge 111 may also be used to generate purified water by removing contaminants from a water source.

The sorbent manifold 101 can selectively direct fluid to either pass through the sorbent cartridge 111 or bypass the sorbent cartridge 111. The sorbent manifold 101 is capable of directing the fluid to enter an inlet 132 of the sorbent cartridge 111 and exit the sorbent cartridge 111 via an outlet 131 of the sorbent cartridge 111. The sorbent manifold 101 can also direct fluid to pass around the sorbent cartridge 111 during ammonia breakthrough or if dialysate pressure exceeds a predetermined range. The sorbent manifold 101 can direct the fluid to flow into a particular direction or multiple directions as needed.

The sorbent manifold 101 can have one or more inlets and one or more outlets through which fluid can enter or exit the sorbent manifold 101. An inlet of the sorbent manifold 101 can be a portion of the sorbent manifold 101 through which fluid and/or gas can be drawn into the sorbent manifold 101. An outlet of the sorbent manifold 101 can be a portion of the sorbent manifold 101 through which fluid or gas can be pulled out of the sorbent manifold 101 in a fluid line, conduit, or fluid passageway of any type. The sorbent manifold 101 can have at least a first inlet 102 and a second inlet 103. The sorbent manifold 101 can have at least a first outlet 104 and a second outlet 105. The first inlet 102, the second inlet 103, the first outlet 104, and the second outlet 105 are not limited to any particular places of the sorbent manifold 101. The inlets and outlets of the sorbent manifold 101 can also be configured at positions that facilitate the formation of passageways to enable fluid communication to the dialysate flow path.

The first and second inlets 102, 103 and first and second outlets 104, 105 of the sorbent manifold 101 may each be an opening at the main body of the sorbent manifold 101, where the first to fourth passageways 113, 114, 115, and 116 are fluidly connectable to corresponding parts of the dialysate flow path through the openings. The openings can be formed by connectors 117, 119, 121, and 118, each having one part attached to the sorbent manifold 101 and a complimentary part attached to the dialysate flow path. Connectors 117, 119, 121, and 118 can also form fluid connections to the dialysate flow path without their respective complimentary parts. Such connectors provide structural features for the sorbent manifold 101 to be fluidly connectable to the dialysate flow path. Connectors 117, 119, 121, and 118 can be fastened onto the sorbent manifold 101 and corresponding parts of the main dialysis flow system. The sorbent manifold 101 can also be connected to the main dialysis system by any one or more of twisting, snapping, plugging, matching protrusions/indents of corresponding structures. Any structural component, means, or method can be applied to connect the sorbent manifold 101 to a main dialysis system The first inlet 102 can be formed by connector 117, the first outlet 104 can be formed by connector 119, the second inlet 103 can be formed by connector 121, and the second outlet 105 can be formed by connector 118. The connectors 117, 118, 119, and 121 can provide for the passage of fluid, gas, or a combination thereof, from one point to another point. The two points can be within or between any one or more of compartments, modules, systems, components, and rechargers, all of any type. The connection can optionally be disconnected and then reconnected.

The sorbent manifold 101 includes a plurality of passageways formed by the fluid entering the sorbent manifold 101. A pump (not shown) can provide a driving force to move fluid through the sorbent manifold 101. The pump may be located at a position in the dialysate flow path upstream to the sorbent manifold 101. The pump may also be located at a position in the dialysate flow path downstream to the sorbent manifold 101. The pump may also be placed in the sorbent manifold 101. There may be one or more pumps that provide the driving force to move fluid through the sorbent manifold 101.

As shown in FIG. 1. The first passageway 113 in the sorbent manifold 101 fluidly connects the first inlet 102 to the first valve 110. The first inlet 102 fluidly connects to a fluid line 136 to receive fluid entering the sorbent manifold 101. The first passageway 113 fluidly connects to the first valve 110 via a port 122. One or more sensors can be selected from a group of sensors consisting of ammonia sensor 106, pressure sensor 107, temperature sensor 108 and conductivity sensor 109, which can be positioned on the first passageway 113 in series to each other. A fluid line 137 can be included as part of the first passageway 113 to fluidly connect the pressure sensor 107 to the other sensors including one or more of the ammonia sensor 106, temperature sensor 108, and conductivity sensor 109. A fluid line 140 can be fluidly connectable to temperature sensor 108 and conductivity sensor 109 as shown in FIG. 2D. A person of skill would understand that the ammonia sensor 106, pressure sensor 107, temperature sensor 108, and conductivity sensor 109 are not limited to a particular order of their positions on the first passageway 113. Ammonia sensor 106 is a device measuring a level of ammonia in the fluid passing by the ammonia sensor 106. The dialysate can flow through or across the ammonia sensor 106 that detects a potentially hazardous condition where the ammonia byproduct of urea breakdown escapes from sorbent cartridge 111. The ammonia sensor 106 may use optical methods to detect a color change of ammonia and/or ammonium sensitive media contained within ammonia sensor 106. The pressure sensor 107 measures the pressure of a gas or fluid in the sorbent manifold 101. If ammonia and/or ammonium are detected, and/or if a pressure level higher than the desired range is detected, control action switches one or more of a first valve 110 and second valve 120 to direct dialysate to bypass the sorbent cartridge 111 through passageway 115. The control action of switching valves is performed by a controller 200 (shown in FIG. 2D) of the sorbent manifold 101. The temperature sensor 108 measures the temperature of a fluid or gas, or a combination thereof in the sorbent manifold 101, and the conductivity sensor 109 measures the electrical conductance of a solution and/or the ion, such as a sodium ion, concentration of a solution. The conductivity sensor 109 can have two electronic heads 109a and 109b.

The first valve 110 can be positioned at downstream of the one or more sensors selected from the group of sensors consisting of ammonia sensor 106, pressure sensor 107, temperature sensor 108 and conductivity sensor 109. The first valve 110 can be a three-way valve with each way attached to a connector fluidly connectable to the first passageway 113 via a port 122, the second passageway 114 via a port 124, and the third passage way 115 via a port 123.

The second passageway 114 fluidly connects the first valve 110 to the first outlet 104 of the sorbent manifold 101. Fluid exiting the first outlet 104 flows into an inlet 132 of the sorbent cartridge 111. In other words, the first outlet 104 of the sorbent manifold 101 is fluidly connectable to the sorbent cartridge 111. A third valve, such as a drain valve 130, can be placed at a position in the dialysate flow path downstream to the first outlet 104 of the sorbent manifold 101 and upstream to the inlet 132 of the sorbent cartridge 111. A drain valve 130 is a valve that can direct the flow of fluid by opening, closing or obstructing one or more pathways to allow the fluid to flow into a drain 112 during priming, disinfection, or draining of the system. As such, fluid exiting the first outlet 104 of the sorbent manifold 101 may first reach the drain valve 130 via a port 125 and then exit the drain valve 130 via a port 126 to flow towards the inlet 132 of the sorbent cartridge 111 along a fluid line 133. Alternatively, the drain valve 130 can selectively direct the fluid exiting the first outlet 104 of the sorbent manifold 101 to a drain 112 via a connector 127 and a fluid line 134.

The third passageway 115 of the sorbent manifold 101 fluidly connects the first valve 110 at port 123 and the second valve 120 at port 128. The first valve 110 can selectively direct fluid into a fluid line 139 to exit the sorbent manifold 101 via a second outlet 105. The fluid line 139 can be a part of the third passageway 115. Fluid exiting the second outlet 105 via connector 118 enters the dialysate flow path at a position downstream to the sorbent manifold 101.

The fourth passageway 116 fluidly connects the second valve 120 to a second inlet 103 of the sorbent manifold 101. The second inlet 103 is fluidly connectable to an outlet 131 of the sorbent cartridge 111. As such, the second inlet 103 and the first outlet 104 of the sorbent manifold 101 can be fluidly connectable to each other through the sorbent cartridge 111. Fluid exiting the first outlet 104 of the sorbent manifold 101 can enter the sorbent cartridge 111 via fluid line 133 fluidly connectable to the sorbent cartridge inlet 132 and exit the sorbent cartridge 111 to enter the second inlet 103 of the sorbent manifold 101 via fluid line 135 fluidly connectable to the sorbent cartridge outlet 131. The second inlet 103 of the sorbent manifold 101 can be a sorbent inlet, which is fluidly connectable to a sorbent line that receives fluid exiting from the sorbent cartridge 111. The second inlet 103 is formed by connector 121 fluidly connectable to the fourth passageway 116, which is fluidly connectable to the second valve 120 via port 138. The second valve 120 is fluidly connectable to the first valve 110 via port 128 attached to the second valve 120 and port 123 attached to the first valve 110. The second valve 120 and first valve 110 is fluid connectable to each other via fluid line 139, which is part of the third passageway 115. Port 128 attached to the second valve 120 is fluidly connectable to connector 129, which is attached to the third passageway 115. Like the first valve 110, the second valve 120 can be a two-way valve, three-way valve, or four-way valve, as understood by a person of ordinary skill in the art.

The sorbent manifold 101 can contain one or more valves positioned therein as a valve assembly or separate valves. The valves can be a device capable of directing the flow of fluid or gas by opening, closing or obstructing one or more pathways to allow the fluid or gas to travel in a path. One or more valves configured to accomplish a desired flow can be configured into a valve assembly. The one or more valves in the sorbent manifold 101 are fluidly connectable to the dialysate flow path. The sorbent manifold 101 can have a first valve 110 and a second valve 120. Additional valves may also be placed in the sorbent manifold 101. The one or more valves may be attached or fixed to the sorbent manifold 101. The one or more valves may become one or more integrated parts of the sorbent manifold 101. For examples, the one or more valves may be welded to the sorbent manifold 101 using known approaches in the art. The one or more valves may also be removably attached to the sorbent manifold 101, and the sorbent manifold 101 may be shaped properly to receive the valves. The sorbent manifold 101 can be shaped as a capital letter "L" in either direction. As shown in FIGS. 1 and 2, the sorbent manifold 101 is shaped as a reversed letter "L" with a second valve 120 positioned close to an intersection of the two perpendicular parts. The sorbent manifold 101 is not limited to a particular shape. For examples, the sorbent manifold 101 may contain a groove complimentary to the shapes of the valves so that the valves may be attached steadily to the sorbent manifold 101. The one or more valves may be placed in different positions within the sorbent manifold 101. For examples, a valve, such as the first valve 110 or the second valve 120, may be fixed to any one of a bottom surface, a side surface, or a top surface of the sorbent manifold 101. The first valve 110 may be a three-way valve and second valve 120 may be a two-way valve as shown in FIG. 1, however, the first valve 110 and the second valve 120 are not limited to a particular type of valve. The first valve 110 and the second valve 120 may be combined as a valve assembly and may also be separately positioned without physically contacting each other. The first valve 110 and second valve 120 may each contain a set of individual valves that can work coordinately to achieve the desired purposes. A person of skill would understand that any suitable type or structure of the one or more valves can be used in the sorbent manifold 101. Further, the valves can be fluidly connected to each other and to the dialysate flow path.

The sorbent manifold 101 can comprise a first valve 110 fluidly connecting a first passageway 113 to a second passageway 114, the first passageway 113 fluidly connectable to a first inlet 102 of the sorbent manifold 101 and the second passageway 114 fluidly connectable to a first outlet 104 of the sorbent manifold 101. The first outlet 104 of the sorbent manifold 101 can be fluidly connectable to an inlet 132 of the sorbent cartridge 111 via valve 130 external to the sorbent manifold 101; second valve 120 inside the sorbent manifold 101 via valve 110 fluidly connecting a third passageway 115 to a fourth passageway 116, the third passageway 115 fluidly connectable to a second outlet 105 of the sorbent manifold 101 via valve 120.

The fourth passageway 116 can be fluidly connectable to a second inlet 103 of the sorbent manifold 101 wherein the second inlet 103 can be fluidly connectable to an outlet 131 of the sorbent cartridge 111. The second inlet 103 can be fluidly connectable to a sorbent line that receives fluid obtained from the sorbent cartridge 111.

The first valve 110 can be positioned between the first passage way 113 and second passageway 114 to fluidly connect the first passageway 113 to the second passageway 114. Spent dialysate can be passed from the first inlet 102 to the first passageway 113, the first valve 110, the second passageway 114, and exit the sorbent manifold 101 via the first outlet 104. Spent dialysate exiting the sorbent manifold 101 can then be directed to pass through the sorbent cartridge 111 and become regenerated after removal of impurities by sorbent materials in the sorbent cartridge 111. The regenerated dialysate can enter the sorbent manifold 101 via the second inlet 103 of the sorbent manifold 101, and exit the sorbent manifold 101 via the second outlet 105 of the sorbent manifold 101 to join the main dialysate flow path.

The sorbent manifold 101 further contains one or more sensors of an ammonia sensor 106, a pressure sensor 107, a temperature sensor 108, and a conductivity sensor 109. The ammonia sensor 106 measures a concentration of ammonia and/or ammonium as an ammonia level in the fluid. Additional sensors can also be placed in sorbent manifold 101, a device for measuring a level of ammonia in the environment. One of ordinal skill will appreciate that any suitable sensor as described herein can be included in the sorbent manifold 101. The sorbent manifold 101 can comprise one or more sensors selected from a group consisting of the ammonia sensor 106, temperature sensor 108, conductivity sensor 109, and pressure sensor 107. Fluid can be directed to flow through the first inlet 102, one or more of ammonia sensor 106, pressure sensor 107, temperature sensor 108, and conductivity sensor 109 to reach the first valve 110. The one or more sensors can be placed in a position upstream of the first valve 110, but are not limited to a specific position or in a specific order in the sorbent manifold 101. The position of the one or more sensors in the flow path can be upstream relative to the one or more valves in the sorbent manifold 101, wherein fluid, gas, or combinations thereof, can flow through the one or more sensors of ammonia sensor 106, pressure sensor 107, temperature sensor 108, and conductivity sensor 109 prior to the first valve 110 during normal operation for dialysis therapy or during priming. The one or more sensors can be used to ensure that the fluid such as dialysate or priming fluid in the flow path is within a proper range of one or more detected fluid characteristic.

The pressure sensor 107 measures pressure of dialysate in the sorbent manifold 101 before an inlet of the sorbent cartridge 111. If the pressure is too high, the dialysate can be directed in the flow path to bypass the sorbent cartridge 111. The temperature sensor 108 measures a temperature of the dialysate. The conductivity sensor 109 measures the electrical conductance of the dialysate and/or the ion, such as a sodium ion, concentration of the dialysate. The pressure sensor 107, temperature sensor 108, and conductivity sensor 109 in the sorbent manifold 101 can be used to ensure that the dialysate in the dialysate flow path is within a proper range of pressure, temperature, and conductivity, respectively.

The sorbent manifold 101 may also include an additional or alternative sensor to detect some or different fluid characteristics of the fluid passing through the sorbent manifold 101. Drain valve 130 located at a position downstream of the first valve 110 can optionally be included either within or outside of the sorbent manifold 101. The drain valve 130 can fluidly connect the first valve 110 to the inlet of the sorbent cartridge 111. The drain valve 130 can selectively direct the fluid to a drain 112 rather than directing fluid towards the sorbent cartridge 111 during draining of the system. The drain valve 130 can be placed in a drain manifold (not shown) separated from the sorbent manifold 101. The drain valve 130 can also be placed within the sorbent manifold 101.

The drain valve 130 of the sorbent manifold 101 is capable of directing the fluid to a drain 112 and is also capable of directing the fluid to flow to sorbent cartridge 111 without flowing into drain 112. The drain valve 130 can selectively direct the flow of fluid by opening, closing or obstructing one or more pathways to allow the fluid to flow into drain 112.

The first valve 110, second valve 120, and drain valve 130 can be controlled by a controller 200, as shown in FIG. 2D. A controller 200 is a device, processor, logic, circuit, or programmable computer which monitors and affects the operational conditions of a given system based on the one or more sensors. The controller 200 can open and close the described valves to direct flow inside and through the sorbent manifold 101. The operational conditions are typically referred to as output variables of the system wherein the output variables can be affected by adjusting certain input variables. The controller 200 can direct actions of a functional component, such as the one or more sensors and valves via signals transferred between the controller 200 and the functional component. The controller 200 can communicate with the valves and sensors by receiving from and sending signals to the valves and sensors. The controller 200 can direct the actions of one or more valves of the first valve 110, second valve 120, and drain valve 130 based on measurements obtained from one or more sensors of the ammonia sensor 106, pressure sensor 107, temperature sensor 108, and conductivity sensor 109. The first valve 110, second valve 120, drain valve 130 and ammonia sensor 106, pressure sensor 107, temperature sensor 108, and conductivity sensor 109. Other functional components in the sorbent manifold 101 can be electronically connected to each other and to the controller 200 by wire, or wirelessly, or a combination thereof.

The controller 200 can collect measurements from the pressure sensor 107, determine whether a pressure level of the dialysate passing through the sorbent manifold 101 is within a desired range. If a pressure level of the dialysate exceeds a desired range, the controller 200 controls one or more of the first valve 110 and the second valve 120 to selectively direct the fluid to bypass the sorbent cartridge 111 through passageway 115 when the controller 200 determines that the pressure level exceeds a desired range. If the pressure level of the dialysate in the sorbent manifold 101 is within the desired range, the controller 200 controls one or more of the first valve 110 and second valve 120 to selectively direct the fluid to one of the fluid paths shown in FIGS. 2A-2B as needed. For example, the controller 200 can direct any one or more of valves 110 or 120 to selectively direct a fluid to bypass the sorbent cartridge 111 when ammonia breakthrough occurs, or if the fluid pressure is above a predetermined range. As such, the sorbent manifold 101 provides a protective mechanism to prevent patient harm due to high pressure or ammonia breakthrough.

The sorbent manifold 101 can comprise a controller 200 (shown in FIG. 2D) in electronic communication with the first valve 110 and the second valve 120; the controller 200 controlling the first valve 110 and second valve 120 to direct the fluid from one of the first inlet 102 and second inlet 103 to one of the first outlet 104 and second outlet 105 of the sorbent manifold 101. During communication, signs, signals, images, sounds, or any data in whole or in part are transferred between the controller 200 and one or more of the first valve 110 and second valve 120 by a wire or wirelessly, or a combination thereof. Any proper means can be used for the controller 200 to communicate with any one or more of the first valve 110 and the second valve 120.

The sorbent manifold 101 can be made of biocompatible materials and can be in any shape suitable to be positioned in the dialysate flow path. The sorbent manifold 101 can be shaped to contain any one or more of the first valve 110, second valve 120, and drain valve 130, and one or more of the ammonia sensor 106, pressure sensor 107, temperature sensor 108, and conductivity sensor 109, and other internal structures, which may include a pump or a heater (not shown in FIG. 1). Alternatively, the sorbent manifold can be formed from molded materials such that the valves are comprised of grooves or channels formed inside the manifold. Similarly, the valve can be incorporated as part of the structure of the sorbent manifold and the passageways formed as channels inside the sorbent manifold. Materials used for making the sorbent manifold 101 can be selected from a group comprising ABS, Lustran, and other similar products proper in the art. The sorbent manifold 101 can be produced using a standard injection molding grade based on a MABS polymer with a well-balanced stiffness, toughness, and high transparency. The materials can be compatible with dialysate and can optionally have sufficient transparency to allow a user to examine passageways and other internal structures contained in the sorbent manifold 101. The sorbent manifold can have compatibility for manufacturing processes such as adhesion or welding.

The sorbent manifold 101 can contain one or more fluid passageways and one or more components such as valves and sensors formed as grooves and channels into a sorbent manifold (not shown). A fluid passageway or channel formed integral to the body of the sorbent manifold provide flow from one location to another location, where the passageway or channels has walls to restrain the fluid or gas within the passageway or channel such that the walls at least in-part surround the fluid or gas and connect the two locations.

The sorbent manifold 101 can have different plastic parts assembled together to form an integrated structure, with a plurality of functional components glued onto the plastic parts inside the sorbent manifold 101. The functional components, such as one or more of the first valve 110, second valve 120, drain valve 130 and one or more of the ammonia sensor 106, pressure sensor 107, temperature sensor 108, and conductivity sensor 109, can also be twisted, snapped, or plugged onto the plastic parts inside the sorbent manifold 101. The sorbent manifold 101 can have a first part, a second part, and a third part, which can be attached together in series to form an integrated structure. One or more of the first part, second part and third part may be removable or permanently connected to a different part of the sorbent manifold 101. The sorbent manifold 101 is not limited to having a particular number of different parts to form the integrated structure. The sorbent manifold 101 can contain a part that can be opened to access internal structures of the sorbent manifold 101. One or more parts of the sorbent manifold 101 may be reversibly sealed to a different part of the sorbent manifold 101.

Different parts of the sorbent manifold 101 can be put together using any suitable means, such as ultrasonic welding, laser welding, or adhesion. The first, second, and third parts can be affixed together using any proper means known in the art. Fluid passageways or internal channels may be completed after the parts being properly positioned together to form the sorbent manifold 101. One part of the sorbent manifold 101 can have a size same or different as that of a different part of the sorbent manifold 101.

The sorbent manifold 101 can be produced using a standard injection molding grade based on a MABS polymer, such as Terlux HD 2802 and Terlux HD 2822, which offers a well-balanced stiffness, toughness, and high transparency, as known in the art. The sensors and the valves or other internal structures can be fixed or attached to the sorbent manifold 101 using techniques suitable to a person of skill in the art. The sensors and the valves can be welded to the main body of the sorbent manifold 101. The first through fourth passageways 113, 114, 115, and 116 can be formed by the lid and main body using ultrasonic or laser welding. The main body of the sorbent manifold 101 can be formed via the use of an energy director. The energy director can be a bead of material molded on the joint surface primarily used to concentrate energy to rapidly initiate the softening and melting of the joint surface. The basic energy design may be incorporated into other joint configurations such as shear joints, step joint, tongue and groove.

Figure 2A:
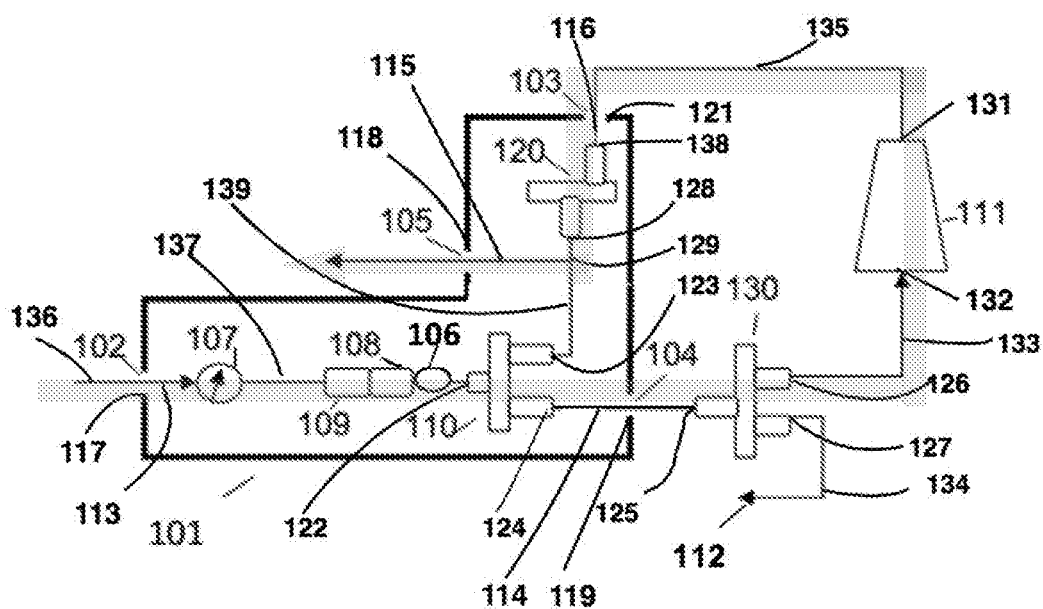
FIG. 2A illustrates exemplary fluid pathways through a sorbent manifold during a treatment mode.
Figure 2B:
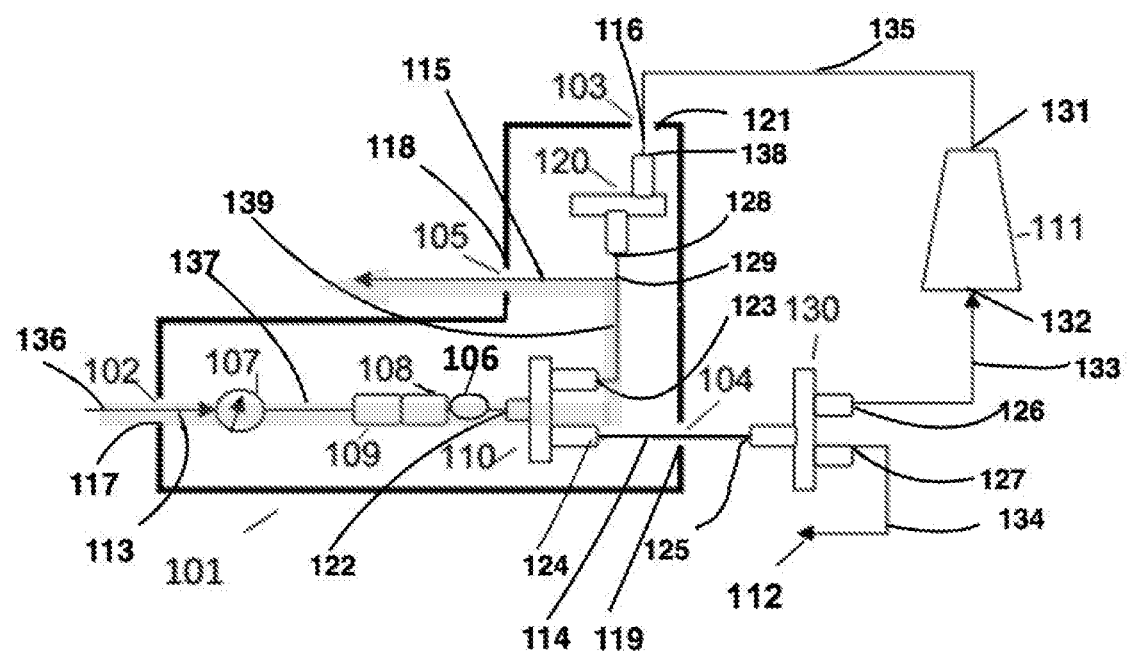
FIG. 2B illustrates exemplary fluid pathways through a sorbent manifold during a sorbent bypass mode.
Figure 2C:
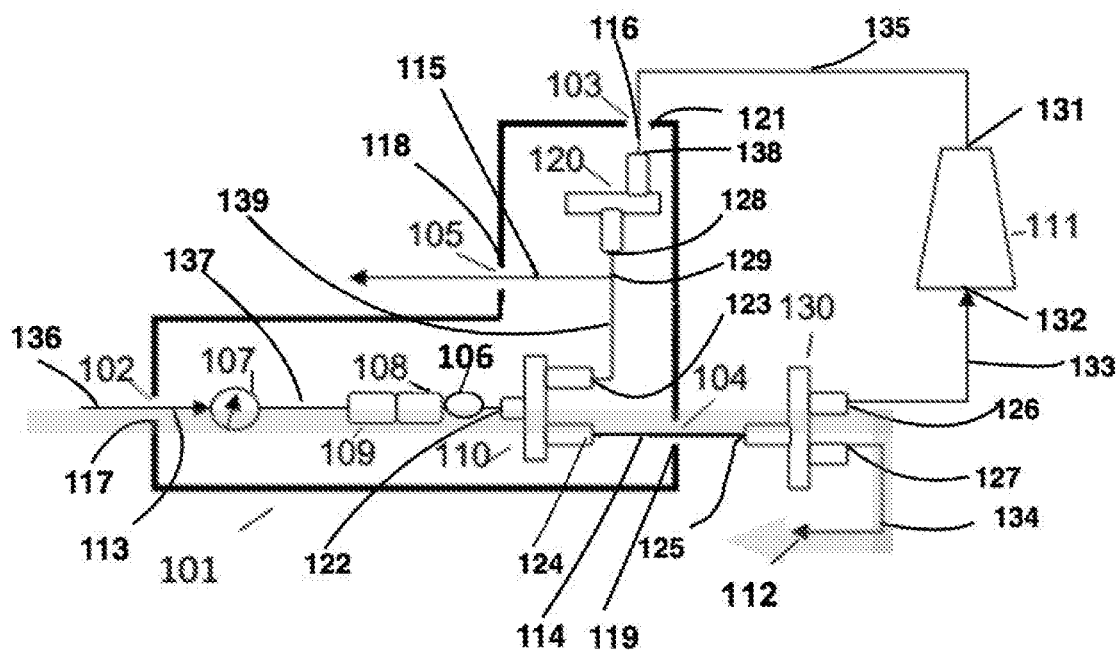
FIG. 2C illustrates exemplary fluid pathways through a sorbent manifold during a system drain mode.
Figure 2D:
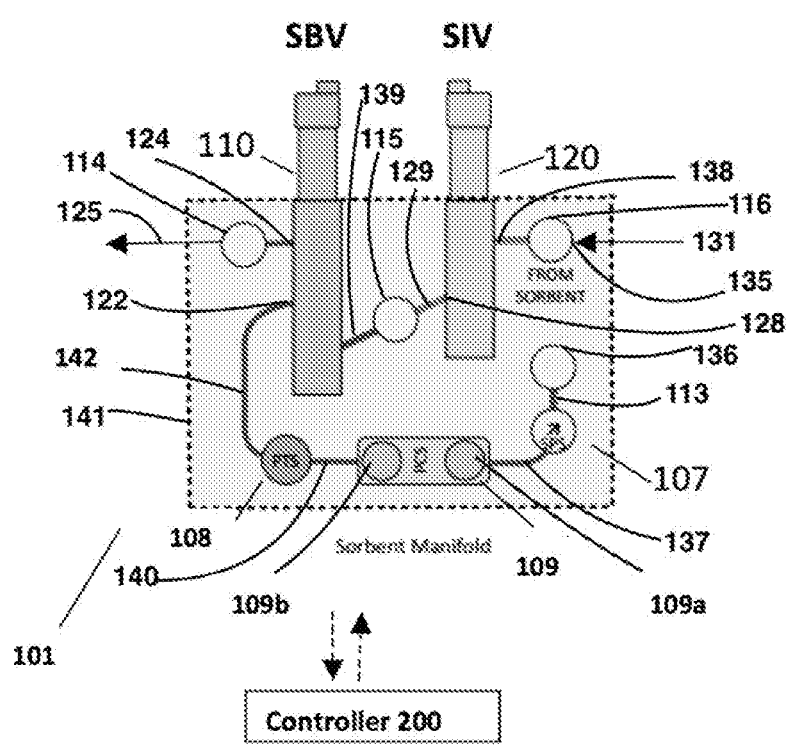
FIG. 2D illustrates exemplary fluid pathways through a sorbent manifold connecting to a drain.

FIGS. 2A-C show pathways in a sorbent manifold 101. FIG. 2A illustrates the fluid paths during a treatment mode. During a treatment mode, the flow path as shown in light gray refers to a valve and flow state in which the sorbent manifold 101 operates to selectively direct fluid exiting the sorbent manifold 101 to pass through a sorbent cartridge 111 positioned downstream to the sorbent manifold 101 and out second outlet 105. The fluid can be dialysate in a dialysate flow path.

FIG. 2B illustrates fluid paths during a sorbent bypass mode in a gray highlighted pathway that selectively directs fluid to pass through the sorbent manifold 101 to bypass a sorbent cartridge 111. The controller 200 of FIG. 2D can control one or more valves based on measurements of one or more sensors in the sorbent manifold 101. FIG. 2C illustrates the fluid paths in gray during a system drain mode. The highlighted paths in gray FIGS. 2A-2C indicate activated passageways based on status of the valves as controlled by a controller 200 as shown in FIG. 2D.

FIG. 2D is a perspective view of a sorbent manifold 101 including the controller 200 that controls the valves and other components of the sorbent manifold 101. An outline 141 of the sorbent manifold 101 is illustrated in FIG. 2D.

During the treatment mode, first valve 110 can be activated and set to a first state such that fluid entering the sorbent manifold 101 through the first inlet 102 can be directed to the first outlet 104 of the sorbent manifold 101 via the first passageway 113 and the second passageway 114 towards an inlet of the sorbent cartridge 111, as shown in FIG. 2A. The first valve 110 fluidly connects the first passageway 113 and the second passageway 114. The first valve 110 and the second valve 120 can be set in the first state that allows the fluid in passageway 113 to flow into the passageway 114 without being diverted towards the second valve 120. Spent dialysate exiting the sorbent manifold 101 can enter the sorbent cartridge 111 inlet, pass through the sorbent materials contained in the sorbent cartridge 111, and exit the sorbent cartridge 111 through outlet 131. As such, impurities and toxins in the spent dialysate can be removed by the one or more sorbent materials in the sorbent cartridge 111. Regenerated dialysate obtained from the sorbent cartridge 111 can enter the dialysate flow path for use. Alternatively, water can enter the sorbent manifold 101 and flow along the passageways 113 and 114 controlled by the first valve 110 and second valve 120.

During the treatment mode, controller 200 as shown in FIG. 2D can collect measurements from the ammonia sensor 106, pressure sensor 107, temperature sensor 108, and conductivity sensor 109 to determine if the measurements are within a desired range. If the measurements from the above sensors are within the desired range, the controller 200 controls the first valve 110 and second valve 120 to continue the treatment mode assuming there are no other adverse signals detected. If the measurements from the above sensors are beyond the desired range, the controller 200 controls the first valve 110 and second valve 120 to switch from the treatment mode to the bypass mode.

During the bypass mode as shown in FIG. 2B, the first valve 110 can be activated and set to a second state and the second valve 120 can set to a second state. As such, the first valve 110 and second valve 120 can selectively direct the fluid entering the first inlet 102 of the sorbent manifold 101 to enter the passageway 115 towards the second outlet 105 of the sorbent manifold 101. The fluid can then exit the sorbent manifold 101 via the second outlet 105. As such, the sorbent manifold 101 can form a flow path connecting the first inlet 102, the first passageway 113, the first valve 110, and a portion of the fluid line between the first valve 110 and the second valve 120, the passageway 115, and the second outlet 105. The bypass mode can be triggered if measurements of an ammonia level or pressure level are outside a predetermined range. The measurements can be obtained from one or more sensors including an ammonia sensor 106, a pressure sensor 107, a temperature sensor 108, and a conductivity sensor 109. The sorbent manifold 101 can also generate an alert to warn a user that the ammonia is detected in the dialysate or the ammonia level exceeds the desired range based on measurements from the ammonia sensor 106. The alert can be any signs, texts, or sounds or a combination thereof. Dialysate can be directed from passageway 113 to passageway 115 when valve 110 is in the normally closed state from port 122 to port 123. The described valve arrangement can be referred to as sorbent bypass or a sorbent bypass mode. Sorbent bypass can be initiated when the pressure exceeds a predetermined threshold or range, such as equal to or greater than about 2,500 mmHg. The sorbent bypass mode can also be initiated during system fluid priming.

FIG. 2C illustrates the fluid passageways in the sorbent manifold 101 fluidly connected to a drain 112. The sorbent manifold 101 can have a drain valve 130 in addition to the first valve 110 and the second valve 120. The drain valve 130 can be positioned external to the sorbent manifold 101 as a component of a drain manifold (not shown). The drain manifold and the sorbent manifold 101 can be combined as one compact structure or separated as two different manifolds. In either configuration, the drain valve 130 can be controlled by a controller 200 (FIG. 2D) to selectively direct the fluid passing through the sorbent manifold 101 to flow to a drain 112. The sorbent manifold 101 can selectively direct the fluid to a drain 112 to drain fluid out of the system, such as after disinfection.

The first valve 110 can be a sorbent bypass valve (SBV) and the second valve 120 can be a sorbent isolation valve (SIV) in FIGS. 2A-2D. A person of skill would understand that the first valve 110 and the second valve 120 are not limited to a certain type of valve. The first valve 110 and the second valve 120 can be any suitable valves. The first valve 110 and the second valve 120 can be 2-way or 3-way valves, or a valve assembly containing multiple valves.

As illustrated in FIGS. 2A-2C, the valves 110 and 120 can be in a specified state to selectively direct fluid through a particular flow path or passageway. In FIG. 2A, port 122 can be connected to port 124, port 125 can be connected to port 126, and port 138 can be connected to port 128, selectively directing fluid through the sorbent cartridge 111. In FIG. 2B, port 122 can be connected to port 123 and port 138 is not connected to port 128, selectively directing fluid through a sorbent bypass pathway. In FIG. 2C, port 122 can be connected to port 124 and port 125 can be connected to port 127 to selectively direct fluid to a drain 112.

FIG. 2D is a perspective view of the sorbent manifold 101 containing a controller 200, the first valve 110 (SBV) and second valve 120 (SIV), one or more of sensors including ammonia sensor 106, pressure sensor 107, temperature sensor 108, and conductivity sensor 109, and the passageways 113, 114, 115, and 116. The controller 200 can contain a processor that receives data from one or more of the sensors including the pressure sensor 107, temperature sensor 108 and conductivity sensor 109. In response to the measurement from the one or more sensors, the controller 200 can determine whether or not to activate any one or more of the first valve 110 and the second valve 120. For the one or more valves that need to be activated, the controller 200 may further determine which state the valves should be set based on the measurements from the one or more sensors. Once a determination is made, the controller 200 can send signals to any one or more of the first valve 110 and the second valve 120 to control opening and closing status of the valves.

The sorbent manifold 101 can comprise a controller 200 in communication with the first valve 110 and the second valve 120; the controller 200 controlling the first valve 110 and second valve 120 to selectively direct the fluid from the first inlet 102 or second inlet 103 to the first outlet 104 or second outlet 105 following the fluid passageways illustrated in FIGS. 2A-2C. An inlet of the sorbent manifold 101 is a portion of the sorbent manifold 101 through which fluid and/or gas can be drawn into the sorbent manifold 101. An outlet of the sorbent manifold 101 can be a portion of the sorbent manifold 101 through which fluid or gas can be pulled out of the sorbent manifold 101 in a fluid line, conduit, or fluid passageway of any type.

The sorbent manifold 101 can comprise the controller 200 which can be programmed to selectively direct the fluid from the first inlet 102 to either the first outlet 104 or to the second outlet 105 based on data from the one or more sensors including pressure sensor 107, temperature sensor 108, and conductivity sensor 109. The controller 200 that has been programmed can perform particular steps according to a series of instructions defined by one or more programs.

The controller 200 can communicate with any one or more of the sensors and valves via signal transferring therebetween. The sensors can include the ammonia sensor 106, pressure sensor 107, temperature sensor 108, conductivity sensor 109, and additional sensors as needed. The valves can include the first valve 110, second valve 120, and additional valves such as the drain valve 130. The signals can be texts, images, sounds, or any data in whole or in-part transferred between the two components via any proper means, such as by a wire or wirelessly, or a combination thereof.

The sorbent manifold 101 can be a component containing one or more fluid passageways and one or more components such as valves and sensors, where one or more valves are controlled by a controller 200 based on measurements of the one or more sensors to direct fluid to either pass through or bypass a sorbent cartridge 111 in a dialysis system. The sorbent manifold 101 can be used as part of a sorbent dialysis system. A sorbent dialysis system contains one or more sorbent cartridges 111 containing one or more sorbent materials for removing impurities, such as urea, from fluid that passes through the sorbent cartridges 111. The sorbent dialysis system can be used for regeneration of spent dialysate or obtaining purified water.

The use of the sorbent manifold 101 can include steps of initiating a dialysis session, pumping the fluid to pass through the sorbent manifold 101 as shown in FIG. 2A, by a pump (not shown) measuring pressure and/or measuring ammonia of the fluid, and if the pressure and/or ammonia level is within a desired range, the fluid will be continued along the flow path shown in FIG. 2A. The fluid can be dialysate.

The dialysate can flow from the first passageway 113 to second passageway 114, optionally flow through a drain valve 130, pass through the sorbent cartridge 111 by flowing from an inlet to an outlet of the sorbent cartridge 111, and enter the sorbent manifold 101 through the second inlet 103 towards the second outlet 105 via the second valve 120 and the third passageway 115 to join the dialysate flow path. If any one or more of the pressure and ammonia level of the fluid is beyond the desired range, the fluid would be directed to bypass the sorbent cartridge 111. If ammonia breakthrough or any other hazardous condition occurs, the dialysate can be directed to bypass the sorbent cartridge 111 to continue the flow path. The sorbent manifold 101 can comprise the at least one sensor including a pressure sensor 107 and wherein the controller 200 selectively directs fluid from the first inlet 102 to the second outlet 105 if the pressure is above a predetermined range. The predetermined range can be obtained by measurement, calculation, or computing means, and programmed or coded into a processor or computer used in the system and methods. The predetermined range can be set to a threshold, including equal to or greater than about 2,500 mmHg. The term "about" can refer to any threshold value close to 2,500 mmHg, including a range of ±15%, ±10%, or ±5%. For example, the threshold value can include any pressure from about 2,125-3,875 mmHg, from about 2,300-2,700 mmHg, from about 2,400-2,600 mmHg, from about 2,450-2,550 mmHg, or from about 2,475-2,525 mmHg.

The controller 200 can receive data of the ammonia level detected by the ammonia sensor 106, and determine whether the dialysate should pass through or bypass the sorbent cartridge 111. If the controller 200 determines that the ammonia level detected by the ammonia sensor 106 is beyond the desired range, the controller 200 can control the first valve 110 and second valve 120 to selectively direct the dialysate to bypass the sorbent cartridge 111. If the controller 200 determines that the ammonia level detected by the ammonia sensor 106 is within the desired range, the controller 200 controls the first valve 110 and second valve 120 to selectively direct the dialysate to pass through the sorbent cartridge 111.

The sorbent cartridge 111 can include multiple material layers including an activated carbon layer, a zirconium phosphate layer, and a urease layer. Any arrangement of the layers is contemplated. The materials can also be mixed together rather than being provided in layers. Because the ability for the zirconium phosphate layer to bind ammonium ions is finite, while the capacity of the urease layer to break down urea into ammonia is not, the capacity of the zirconium phosphate layer may be exceeded. In such a case, excess ammonium ions can be caused to pass through the sorbent cartridge 111 and remain in the dialysate.

A method can include steps of pumping a dialysate from a dialyzer outlet, through a dialysate flow path to the first inlet 102 of the sorbent manifold 101, pumping the dialysate through the first passageway 113 and second passageway 114 to the first outlet 104 of the sorbent manifold 101, pumping the dialysate from the first outlet 104 of the sorbent manifold 101 to an inlet of the sorbent cartridge 111, pumping the dialysate from an outlet of the sorbent cartridge 111 to the second inlet 103 of the sorbent manifold 101, pumping the dialysate from the second inlet 103 to the second outlet 105 of the sorbent manifold 101 and into the dialysate flow path downstream of the sorbent cartridge 111, and pumping the dialysate to a dialyzer inlet. Pumping a dialysate means moving dialysate through a flow path with a pump.

Figure 3:
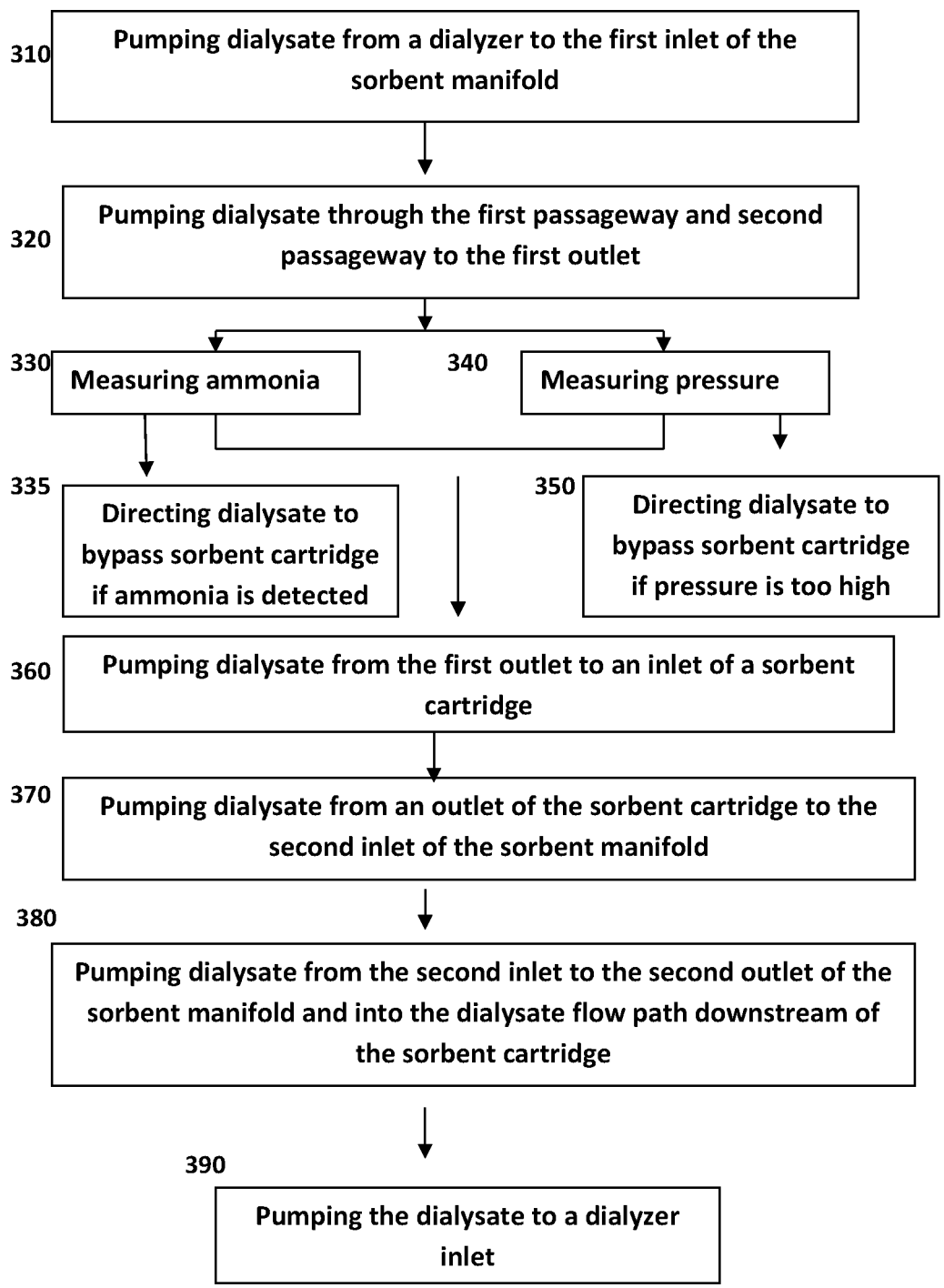
FIG. 3 is a flow chart showing operation of a sorbent manifold.

As shown in FIG. 3, the use of the sorbent manifold 101 can include steps 310-390. In particular, at step 310, dialysate is pumped from a dialyzer to the first inlet 102 of the sorbent manifold 101. As known in the art, a dialyzer is a cartridge or container with two flow paths separated by semi-permeable membranes, where one flow path is for blood and one other flow path is for dialysate. The membranes can be in hollow fibers, flat sheets, or spiral wound or other conventional forms known to those of skill in the art. Membranes can be selected from any one or combination of materials: polysulfone, polyethersulfone, poly (methyl methacrylate), modified cellulose, or other materials known to those skilled in the art. A dialyzer has an inlet for fluid to enter the cartridge and an outlet for fluid to exit the cartridge. Dialysate is a fluid into or out of which solutes from a fluid to be dialyzed diffuse through a membrane. A dialysate typically contains electrolytes close in concentration to the physiological concentration of electrolytes found in blood. "Dialysate flow path" refers to a fluid pathway or passageway that conveys a fluid, such as dialysate and is configured to form at least part of a fluid circuit for peritoneal dialysis, hemodialysis, hemofiltration, hemodiafiltration or ultrafiltration.

At step 320, dialysate is pumped through the first passageway 113 and second passageway 114 to the first outlet 104 of the sorbent manifold 101. At steps 330 and 340, the fluid can be measured by the one or more sensors for pressure level and ammonia level. Steps 330 and 340 can be parallel to each other. The measurement can be sent to a controller 200 wirelessly or via wire or any other means proper in the art.

At step 330, an ammonia sensor 106 can measure an ammonia concentration in the dialysate downstream of the sorbent cartridge 111. At step 335, one or more of the first valve 110 and second valve 120 can be switched to bypass the sorbent cartridge 111 in response to ammonia in the dialysate. If the ammonia is detected in the dialysate by an ammonia sensor 106, a controller 200 can perform control action to switch the first valve 110 and second valve 120 in response to ammonia detected in the dialysate. The ammonia sensor 106 is placed in the sorbent manifold 101 upstream of the sorbent cartridge 111. The valves can be changed the from a first position to a second position so that a fluid can be directed to a direction defined by the second position from a direction defined by the first position. The first position and second position of a valve can be an opened position and a closed position.

If the ammonia is not detected in the dialysate, a controller 200 can control one or more of the first valve 110 and second valve 120 in response to lack of ammonia in the dialysate to allow the dialysate to enter the sorbent cartridge 111 positioned downstream to the sorbent manifold 101. If ammonia breakthrough occurs, the dialysate can be forced to bypass the sorbent cartridge 111 to prevent ammonia formation and to avoid harmful outcome to the patient. The sorbent manifold 101 can also generate an alert if ammonia is detected in the dialysate.

At step 340, a pressure sensor 107 can measure a pressure of the fluid passing through the sorbent manifold 101. The pressure sensor 107 can measure the pressure in the dialysate in the first passageway 113, and the controller 200 can switch one or more of the first valve 110 and second valve 120 to allow pumping fluid from the first inlet 102 to the second outlet 105 of the sorbent manifold 101. The fluid can then be selectively directed to the sorbent cartridge 111 or back to the main dialysate flow path in response to the pressure measured by the pressure sensor 107. Switching the first valve 110 and second valve 120 in response to the pressure in the dialysate can be performed by a controller 200 in communication with a pressure sensor 107 in the first passageway 113 of the sorbent manifold 101. If the measurement of the pressure sensor 107 exceeds a predetermined range at step 350, the controller 200 can be programmed to switch one or more of the first valve 110 and second valve 120 in response to the pressure so that the fluid can be selectively directed back to the main dialysate flow path, bypassing the sorbent cartridge 111.

A pressure in the dialysate can be measured by a pressure sensor 107 in the first passageway 113, and controller 200 can switch one or more of the first valve 110 and second valve 120 to pump the fluid from the first inlet 102 to the first outlet 104 of the sorbent manifold 101 towards the second outlet 105, in response to a pressure over a predetermined level. For example, controller 200 can switch the first valve 110 and second valve 120 to pump the fluid from the first inlet 102 to the second outlet 105 of the sorbent manifold 101 in response to a pressure over a predetermined level.

If the measurement of the pressure level in the fluid is within the predetermined range, at step 360, the controller 200 can selectively direct the fluid to continue in a flow path after passing through the sorbent cartridge 111. Pressure in the dialysate can be measured by a pressure sensor 107 in the first passageway 113, and the controller 200 can switch one or more of the first valve 110 and second valve 120 to pump the fluid from the first inlet 102 to the first outlet 104 of the sorbent manifold 101 towards a sorbent cartridge 111 via the drain valve 130, in response to a pressure within a predetermined level. The controller 200 can also switch one or more of the first valve 110, second valve 120, and drain valve 130 to pump the fluid from the first inlet 102 to the second outlet 105 of the sorbent manifold 101 to join the main flow path such that the fluid does not pass through a sorbent cartridge 111 or the drain valve 130, in response to a pressure exceeding a predetermined level.

In this manner, the controller 200 can control whether the pressure and ammonia level of the fluid is within a desired range based on or in response to a sensor measurement. If both of the pressure and ammonia level are within their perspective desired ranges, the fluid can continue as described in steps 360-390. At least one of the pressure and ammonia level can be measured. Based on the measurement of the pressure and/or ammonia level, the controller 200 can determine whether the measurement is within a desired range. At step 360, the dialysate can be pumped from the first outlet 104 to an inlet 132 of a sorbent cartridge 111. At step 370, the dialysate can be pumped from an outlet of the sorbent cartridge 111 to the second inlet 103 of the sorbent manifold 101. At step 380, the dialysate can be pumped from the second inlet 103 to the second outlet 105 of the sorbent manifold 101 and into the dialysate flow path downstream to the sorbent manifold 101. The second inlet 103 can be a sorbent inlet receiving fluid from the sorbent cartridge 111. At step 390, the dialysate can be pumped into a dialyzer through an inlet thereof. The dialysate thus flows into the dialyzer via the dialyzer inlet and exits the dialyzer via the dialyzer outlet. If controller 200 determines that the pressure level measured at step 340 is too high, the fluid can be directed to bypass the sorbent cartridge at step 350. If the controller 200 determines that an undesirable ammonia level measured at step 330 is detected, the fluid can be directed to bypass the sorbent cartridge. If ammonia breakthrough occurs, ammonia can be detected in the dialysate entering the sorbent manifold 101 via the first inlet 102. Upon detecting ammonia, controller 200 can control the drain valve 120 to direct the dialysate to flow into the drain 112 without re-entering the main dialysate flow path.

Figure 4:
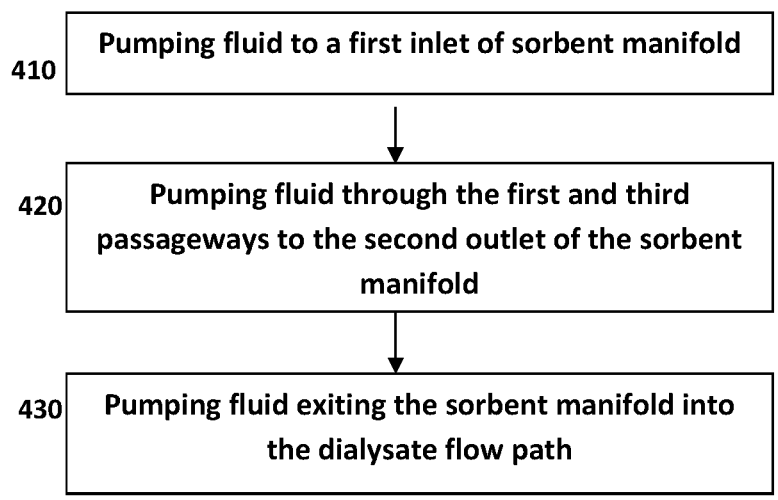
FIG. 4 is a flow chart showing operation of a sorbent manifold.

In FIG. 4, the use of the sorbent manifold 101 can be operated in a sorbent bypass mode shown in steps 410-430. During a sorbent bypass mode, controller 200 of a sorbent manifold 101 can selectively direct fluid that passes through the sorbent manifold 101 to bypass a sorbent cartridge 111 by controlling one or more valves in response to measurements of one or more sensors in the sorbent manifold 101 and the sorbent cartridge 111 fluidly connectable to the sorbent manifold 101. At step 410, fluid can be pumped from the main dialysate flow path to the first inlet 102 of the sorbent manifold 101. At step 420, fluid is pumped through the first passageway 113 and third passageway 115 to the second outlet 105 of the sorbent manifold 101. At steps 430, the fluid is pumped from the second outlet 105 to continue the main dialysate flow path. As such, the fluid does not pass through the sorbent cartridge 111 prior to rejoining the main dialysate flow path.

The sorbent manifold 101 can be operated in the sorbent bypass mode during priming or in response to a pressure, temperature or ammonia concentration outside of a predetermined range. The sorbent bypass mode can also be in operation during cleaning and disinfection of the dialysis system. The sorbent bypass mode and the treatment mode can be switched from one to the other intermittently during the system drain mode as noted above to clean up fluid in the fluid line between the first valve 110 and second valve 120. A person of skill would understand that the sorbent bypass mode is not limited for the above purposes.

The first valve 110 and second valve 120 are integrated in a compact structure of the sorbent manifold 101 and can be controlled by a controller 200 to be selectively in an opened or closed status so that the sorbent manifold 101 can be operated in a desired mode. The controller 200 can control the sorbent manifold 101 to operate in a treatment mode and change from the treatment mode to sorbent bypass mode. The valve switch resulting in the treatment mode and bypass mode of operation can be effectuated by any means known in the art using mechanical force or electronic control. A user can interact with the controller 200 through a user interface to enter specific command directing the valves to switch to a particular state of operation. The controller 200 can also switch the sorbent manifold 101 from the treatment mode to the bypass mode or from the bypass mode to the treatment mode based on measurements from the one or more sensors including pressure sensor 107, temperature sensor 108, and conductivity sensor 109. In other words, the sorbent manifold 101 does not need a user to standby monitoring the mode of operation and determine whether and when to switch to a different mode. Instead, the sorbent manifold 101 can determine by the controller 200 which mode of operation is proper at a particular moment. As such, the dialysis system with the sorbent manifold 101 can further eliminate a need of a trained professional to operate the dialysis system.

Figure 5A:
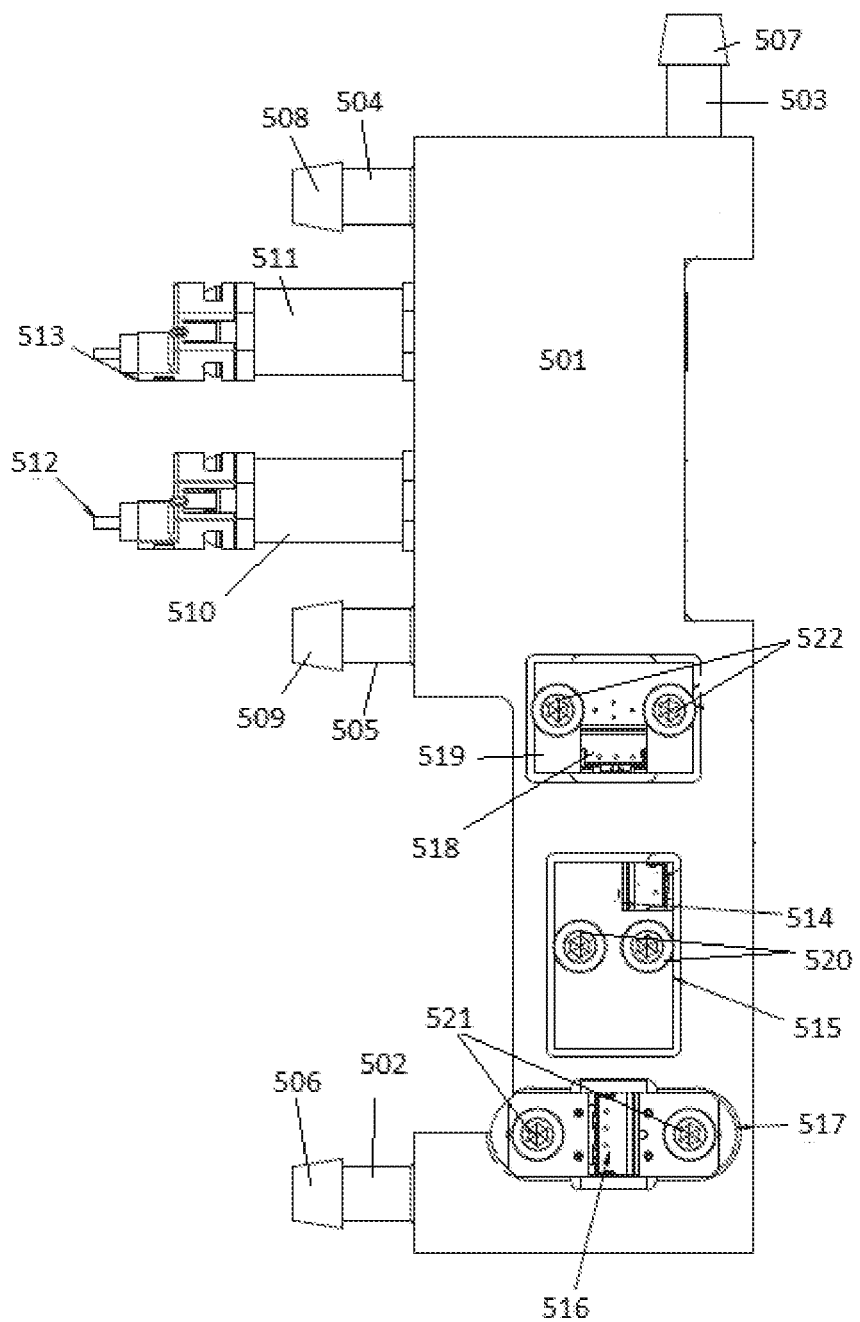
FIG. 5A is a perspective view of a sorbent manifold.
Figure 5B:
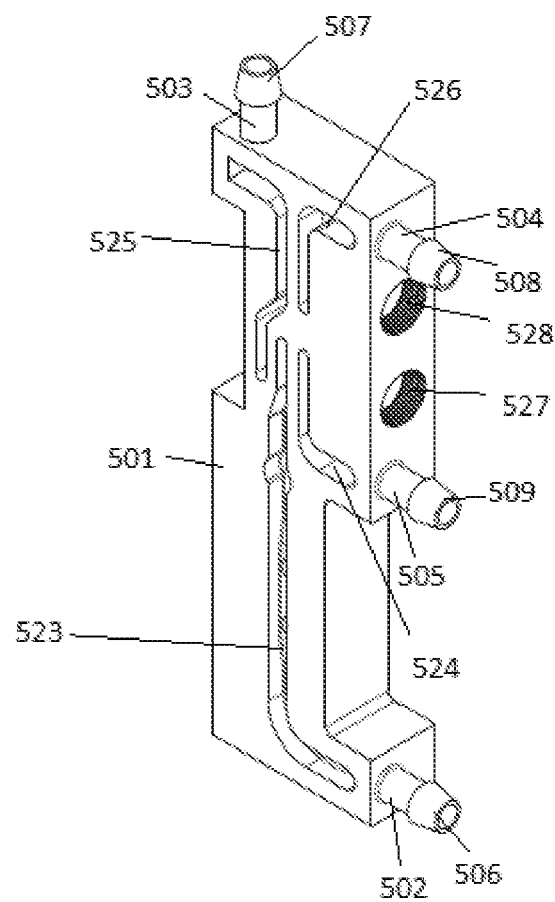
FIG. 5B is a view of a sorbent manifold showing fluid passageways.
Figure 5C:
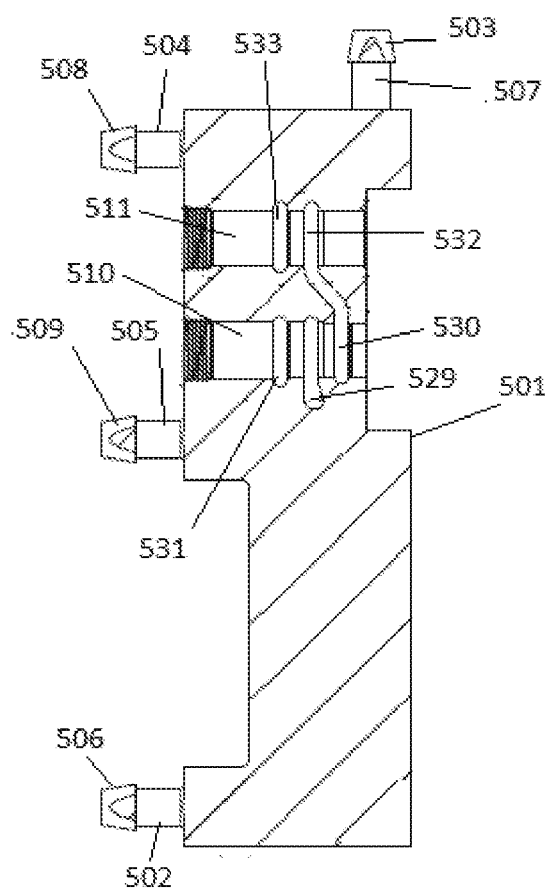
FIG. 5C is a cross sectional view of a sorbent manifold.

FIGS. 5A-C are drawings of a non-limiting embodiment of a sorbent manifold 501. FIG. 5A is a perspective view of the sorbent manifold 501, FIG. 5B illustrates the passageways of the sorbent manifold 501, and FIG. 5C is a cross section of the sorbent manifold 501.

As illustrated in FIGS. 5A-C, the sorbent manifold 501 includes a first inlet 502, a second inlet 504, a first outlet 505 and a second outlet 503. Connector 506 on inlet 502, connector 507 on outlet 503, connector 508 on inlet 504, and connector 509 on outlet 505 can facilitate connection to tubing in a dialysate flow path. Valves 510 and 511 control the movement of fluid through the sorbent manifold 501. A controller (not shown) can control the valves 510 and 511 through controls 512 and 513. One or more sensors, including temperature sensor 516, pressure sensor 514, and ammonia sensor 518 can be included in the fluid passageways. Circuit boards 517, 515, and 519 are in electronic communication with the sensors and a controller (not shown). The sensors and circuit boards can be mounted on the sorbent manifold 501 by screws 520, 521, and 522, or by any other method known in the art.

As illustrated in FIG. 5B, the sorbent manifold 501 can include a first passageway 523 from the first inlet 502 to a first valve 510. The first valve 510 (not shown in FIG. 5B) can be inserted through hole 527 in the sorbent manifold 501. The first valve 510 can selectively direct fluid from the first passageway 523 to either a second passageway 524 through conduit 529 illustrated in FIG. 5C and the first outlet 505, or to a second valve 511 (not shown in FIG. 5B), which can be inserted through hole 528 via conduit 532. O-rings 531 and 533, illustrated in FIG. 5C, can be included to secure the valves 510 and 511 in place. The first outlet 505 can be fluidly connected to an inlet of a sorbent cartridge, as described. During treatment, fluid can be selectively directed from the first inlet 502 to the first outlet 505 for regeneration by the sorbent cartridge. If any fluid characteristic is not within a predetermined range, the first valve 510 can be switched to selectively direct fluid to second outlet 503 through fluid passageway 525, bypassing the sorbent cartridge.

Second inlet 504 can be fluidly connected to an outlet of the sorbent cartridge. Fluid from the sorbent cartridge can enter the sorbent manifold through second inlet 504 into passageway 526. Passageway 526 can also connect to the second valve 511, which can prevent fluid movement through passageway 526 during a sorbent bypass mode, or direct fluid into passageway 525 and second outlet 503. The second outlet 503 can be fluidly connected to the dialysate flow path (not shown).

The fluid passageways 523, 525, and 526 can be formed from molded materials such that the passageways 523, 525, and 526 are grooves or channels formed within the sorbent manifold 501. The passageways 523, 525, and 526 can thus form part of a unitary body of the sorbent manifold 501, eliminating extraneous fluid lines or tubes. By reducing the amount of fluid lines or tubing used in the dialysis system, the unitary sorbent manifold 501 can reduce kinking, which is common in known dialysis systems. The unitary sorbent manifold also eliminates the need to replace tubing, increasing the durability and ease of manufacturing of the system.

One skilled in the art will understand that various combinations and/or modifications and variations can be made in the described systems and methods depending upon the specific needs for operation. Moreover, features illustrated or described as being part of an aspect of the invention may be used in the aspect of the invention, either alone or in combination.

We claim:

1. A sorbent manifold for a sorbent dialysis system, comprising:
   a first inlet connector, a first outlet connector, a second inlet connector, and a second outlet connector;
   a three-way sorbent bypass valve including an inlet port, a first outlet port, and a second outlet port;
   a two-way sorbent isolation valve including an inlet port and an outlet port;
   a first passage connecting the first inlet connector to the inlet port of the three-way sorbent bypass valve;
   at least one sensor disposed in the first passage;
   a second passage connecting the first outlet port of the three-way sorbent bypass valve to the first outlet connector;
   a fifth passage connecting the second outlet port of the three-way sorbent bypass valve to the outlet port of the two-way sorbent isolation valve;
   a third passage connecting the fifth passage to the second outlet connector; and
   a fourth passage connecting the inlet port of the two-way sorbent isolation valve to the second inlet passage.

2. The sorbent manifold of claim 1, wherein the at least one sensor is selected from a group consisting of an ammonia sensor, a conductivity sensor, a temperature sensor, and a pressure sensor.

3. The sorbent manifold of claim 1, wherein the first outlet connector is fluidly connectable to a drain valve prior to reaching a sorbent cartridge inlet, the drain valve selectively directing fluid to the sorbent cartridge inlet or to a drain line.

4. The sorbent manifold of claim 3, wherein the drain valve is positioned in a separate drain manifold.

5. The sorbent manifold of claim 1, wherein the first outlet connector and the second inlet connector are fluidly connectable to each other through a sorbent cartridge inlet and outlet.

6. The sorbent manifold of claim 1, wherein the three-way sorbent bypass valve and the two-way sorbent isolation valve are configured to selectively direct fluid from the first inlet connector to the first outlet connector and from the second inlet connector to the second outlet connector in a treatment mode.

7. The sorbent manifold of claim 1, wherein the three-way sorbent bypass valve and the two-way sorbent isolation valve are configured to selectively direct the fluid from the first inlet connector to the second outlet connector in a sorbent bypass mode.

8. A sorbent manifold system, comprising:
   a first inlet connector, a first outlet connector, a second inlet connector, and a second outlet connector;
   a three-way sorbent bypass valve including an inlet port, a first outlet port, and a second outlet port;
   a two-way sorbent isolation valve including an inlet port and an outlet port;
   a first passage connecting the first inlet connector to the inlet port of the three-way sorbent bypass valve;
   at least one sensor disposed in the first passage;
   a second passage connecting the first outlet port of the three-way sorbent bypass valve to the first outlet connector;
   a fifth passage connecting the second outlet port of the three-way sorbent bypass valve to the outlet port of the two-way sorbent isolation valve;
   a third passage connecting the fifth passage to the second outlet connector; and
   a fourth passage connecting the inlet port of the two-way sorbent isolation valve to the second inlet passage;

a controller controlling the three-way sorbent bypass valve and the two-way sorbent isolation valve to direct fluid to either pass through a sorbent cartridge in the sorbent dialysis system or bypass the sorbent cartridge based on measurements of the at least one sensor; and the second inlet connector fluidly connectable to an outlet of the sorbent cartridge, wherein the controller controls the fluid to enter the second inlet connector from the outlet of the sorbent cartridge.

9. The sorbent manifold system of claim 8, the controller in communication with the three-way sorbent bypass valve and the two-way sorbent isolation valve; the controller controlling the three-way sorbent bypass valve and the two-way sorbent isolation valve to direct the fluid from one of the first inlet connector and the second inlet connector to one of the first outlet connector and the second outlet connector.

10. The sorbent manifold system of claim 9, wherein the controller is programmed to selectively direct the fluid from the first inlet connector to either the first outlet connector or second outlet connector based on data from the at least one sensor.

11. The sorbent manifold system of claim 10, wherein the at least one sensor includes a pressure sensor; and wherein the controller selectively directs fluid from the first inlet connector to the second outlet connector if a pressure is above a predetermined range.

12. The sorbent manifold of claim 11, wherein the predetermined range is a pressure equal to or greater than about 2,500 mmHg.

13. The sorbent manifold system of claim 9, the controller in communication with an ammonia sensor downstream of the sorbent cartridge; and wherein the controller selectively directs fluid from the first inlet connector to the second outlet connector if ammonia is detected by the ammonia sensor.

14. The sorbent manifold system of claim 9, the controller controlling the three-way sorbent bypass valve and the two-way sorbent isolation valve to direct the fluid from the first inlet connector to the first outlet connector and from the second inlet connector to the second outlet connector.

* * * * *